US012790599B2

(12) United States Patent
Walker et al.

(10) Patent No.: US 12,790,599 B2
(45) Date of Patent: *Nov. 10, 2026

(54) REVERSE TRANSCRIPTASE VARIANTS

(71) Applicant: Watchmaker Genomics, Inc., Boulder, CO (US)

(72) Inventors: Julie Walker, Wheat Ridge, CO (US); Bjarne Faurholm, Cape Town (ZA); Ross Wadsworth, Cape Town (ZA); Brian A. Kudlow, Boulder, CO (US)

(73) Assignee: Watchmaker Genomics, Inc., Boulder, CO (US)

( * ) Notice: Subject to any disclaimer, the term of this patent is extended or adjusted under 35 U.S.C. 154(b) by 230 days.

This patent is subject to a terminal disclaimer.

(21) Appl. No.: 18/844,810

(22) PCT Filed: Mar. 7, 2023

(86) PCT No.: PCT/US2023/063817

§ 371 (c)(1),
(2) Date: Sep. 6, 2024

(87) PCT Pub. No.: WO2023/172888

PCT Pub. Date: Sep. 14, 2023

(65) Prior Publication Data

US 2025/0197821 A1 Jun. 19, 2025

Related U.S. Application Data

(63) Continuation of application No. 17/940,797, filed on Sep. 8, 2022, now Pat. No. 11,639,499.

(60) Provisional application No. 63/317,634, filed on Mar. 8, 2022.

(51) Int. Cl.
*C12N 9/12* (2006.01)

(52) U.S. Cl.
CPC .... *C12N 9/1276* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 6,210,891 | B1 | 4/2001 | Nyren et al. |
| 6,306,597 | B1 | 10/2001 | Macevicz |
| 6,828,100 | B1 | 12/2004 | Ronaghi |
| 6,833,246 | B2 | 12/2004 | Balasubramanian |
| 6,911,345 | B2 | 6/2005 | Quake et al. |
| 7,078,208 | B2 | 7/2006 | Smith et al. |
| 7,232,656 | B2 | 6/2007 | Balasubramanian et al. |
| 7,598,035 | B2 | 10/2009 | Macevicz |
| 7,835,871 | B2 | 11/2010 | Kain et al. |
| 7,960,120 | B2 | 6/2011 | Rigatti et al. |
| 8,209,130 | B1 | 6/2012 | Kennedy et al. |
| 8,835,148 | B2 | 9/2014 | Janulaitis et al. |
| 9,580,698 | B1 | 2/2017 | Xu et al. |
| 9,683,251 | B2 | 6/2017 | Janulaitis et al. |
| 10,287,614 | B2 | 5/2019 | Janulaitis et al. |
| 10,358,670 | B2 | 7/2019 | Janulaitis et al. |
| 11,639,499 | B1 | 5/2023 | Walker et al. |
| 12,503,690 | B1 | 12/2025 | Walker et al. |
| 2002/0090618 | A1 | 7/2002 | Smith et al. |
| 2006/0024681 | A1 | 2/2006 | Smith et al. |
| 2006/0292611 | A1 | 12/2006 | Berka et al. |
| 2007/0114362 | A1 | 5/2007 | Feng et al. |
| 2008/0227661 | A1 | 9/2008 | Hogrefe et al. |
| 2011/0009278 | A1 | 1/2011 | Kain et al. |

FOREIGN PATENT DOCUMENTS

| | | | |
|---|---|---|---|
| EP | 3093341 | A1 | 11/2016 |
| JP | 2003-526378 | A | 9/2003 |
| JP | 2009-504162 | A | 2/2009 |
| WO | WO 01/68895 | A1 | 9/2001 |
| WO | WO 2018/110595 | A1 | 6/2018 |
| WO | WO 2022/009116 | A1 | 1/2022 |
| WO | WO 2022/020371 | A2 | 1/2022 |

OTHER PUBLICATIONS

Invitation to Pay Additional Fees for Application No. PCT/US2023/063817, mailed Jun. 6, 2023.
International Search Report and Written Opinion for Application No. PCT/US2023/063817, mailed Aug. 4, 2023.
International Preliminary Report on Patentability for Application No. PCT/US2023/063817, mailed Sep. 19, 2024.
Baba et al., Further increase in thermostability of Moloney murine leukemia virus reverse transcriptase by mutational combination. Protein Eng Des Sel. Aug. 1, 2017;30(8):551-557. doi: 10.1093/protein/gzx046.
Karlsson, Counting Molecules in cell-free DNA and single cells RNA. Karolinska Institute of Stockholm, Sweden. 2016. 52 pages.
UNIPARC Submission; Accession No. UPI00004ABOA8, USPTO ID: AAU74989; Sep. 22, 2004. 2 pages.
Partial European Search Report for Application No. 23767597.0, mailed Feb. 17, 2026.
Extended European Search Report for Application No. 23767597.0, mailed May 11, 2026.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

(Continued)

*Primary Examiner* — Manjunath N Rao
*Assistant Examiner* — Jae W Lee
(74) *Attorney, Agent, or Firm* — Choate, Hall & Stewart LLP; Stephanie L. Schonewald; Meaghan E. Bychowski

(57) ABSTRACT

The present invention provides MMLV reverse transcriptase enzymes with increased thermal stability as compared with wild type MMLV and AMV reverse transcriptases. The improved thermal stability allows for reverse transcription of RNA to cDNA at temperatures above 37° C., thereby reducing error rates introduced during cDNA synthesis. As a result, the reverse transcriptases of the invention allow for increased accuracy in the determination of transcriptomes of living organisms.

22 Claims, 17 Drawing Sheets

Specification includes a Sequence Listing.

(56) References Cited

OTHER PUBLICATIONS

Oscorbin et al., M-MuLV reverse transcriptase: Selected properties and improved mutants. Comput Struct Biotechnol J. Nov. 22, 2021:19:6315-6327. doi: 10.1016/j.csbj.2021.11.030. eCollection 2021.
UNIPROT Submission; Accession No. A7UJ21; A7UJ21_MULV. Sequence Version 1, Entry Version 134, Jan. 28, 2026. 8 pages.
UNIPROT Submission; Accession No. A1Z651; POL_XMRV6. Sequence Version 1, Entry Version 118, Jan. 28, 2026. 17 pages.
UNIPROT Submission; Accession No. Q9YK99; Q9YK99_MULV. Sequence Version 1, Entry Version 157, Jan. 28, 2026. 8 pages.
UNIPROT Submission; Accession No. A0A140D496; A0A140D496_MULV. Sequence Version 1, Entry Version 56, Jan. 28, 2026. 9 pages.
UNIPROT Submission; Accession No. P26808; POL_MLVFP. Sequence Version 1, Entry Version 144, 15 pages.

| RT | FSS temp | Efficiency score |
|---|---|---|
| WMG RTIII | 50 | 96 |
| WMG RTIII | 60 | 99 |
| prod-ana RT | 50 | 92 |
| prod-ana RT | 60 | 99 |
| Maxima | 50 | 125 |
| Maxima | 60 | 160 |

FIG. 1B

| IP name | Tagg (C) | % CV |
|---|---|---|
| prod-dnd | 60.7 | 0.25 |
| prod-amg | 61.6 | 0.08 |
| prod-ajw | 62.9 | 0.1 |
| prod-bih | 63.1 | 0.68 |
| prod-cnc* | 65.9 | 0.67 |
| prod-ana | 68.2 | 0.69 |

FIG. 3D

REVERSE TRANSCRIPTASE VARIANTS

RELATED APPLICATIONS

This application is a national stage filing under 35 U.S.C. § 371 of International Application No. PCT/US2023/063817, filed Mar. 7, 2023, which is a continuation of U.S. application Ser. No. 17/940,797, filed Sep. 8, 2022, now U.S. Pat. No. 11,639,499, issued May 2, 2023, and which claims the benefit of U.S. Provisional Application No. 63/317,634, filed Mar. 8, 2022. U.S. application Ser. No. 17/940,797, filed Sep. 8, 2022, claims the benefit of U.S. Provisional Application No. 63/317,634, filed Mar. 8, 2022. The entire contents of these applications are incorporated by reference herein.

REFERENCE TO AN ELECTRONIC SEQUENCE LISTING

The contents of the electronic sequence listing (W109470002US02-SEQ-ARM.xml; Size: 31,156 bytes; and Date of Creation: Sep. 6, 2024) is herein incorporated by reference in its entirety.

TECHNICAL FIELD

The present invention relates to reverse transcriptases.

BACKGROUND

The transcriptome refers to the RNA transcripts of a cell or organism at a given time. Knowledge of the transcriptome reveals active cellular processes and can provide information about cell regulation, growth and dysfunction.

Transcriptome analysis typically involves microarray technology and, more commonly, next-generation sequencing technologies (e.g., RNA-Seq). Common objectives of RNA-Seq are to detect all of the diverse transcripts present, including mRNA and non-coding RNA, as well as to detect splice variants, mutations, mobile genetic elements, and expression levels during various stages of development or under various conditions. Transcriptomics and RNA-Seq have application in diagnostics, disease profiling, pathogen detection, evolutionary biology, and other areas of research. For example, RNA-Seq can potentially identify genes involved in resistance to environmental stresses, such as drought resistance in crops. In another example, transcriptomic profiling can provide information on mechanisms of drug resistance, potentially revealing strategies for combating hospital-acquired antibiotic-resistant infections.

Typically, in an RNA-Seq workflow, RNA is first used to synthesize stable complementary DNA (cDNA) copies of target RNA through a reverse transcription reaction. Reverse transcriptase enzymes are the typical enzymes used to synthesize cDNA from an RNA. Because reverse transcriptases have no proofreading ability, unlike DNA polymerases, higher reaction temperatures for reverse transcription reactions are generally desirable. This is because the higher temperatures reduce off-target primer binding. In addition, higher temperatures reduce secondary structures in RNA, which can cause steric hinderance to the RT, thus truncating transcripts. However, common commercially available reverse transcriptases, for example Moloney murine leukemia virus (MMLV), Superscript II, and avian myeloblastosis virus (AMV), begin to lose efficiency above 37° C. As a result, the high error rate allows mutations to accumulate at an accelerated rate in comparison to proofread forms of synthesis. For example, AMV reverse transcriptases typically have error rates of 1 in 17,000 bases and MMLVs typically have errors rates of 1 in 30,000 bases. As a result, commercially available reverse transcriptases impede accurate determination of a transcriptome.

SUMMARY

The present invention provides modified reverse transcriptase enzymes with increased thermal stability, increased solubility and reduced qPCR inhibition as compared with conventional commercial reverse transcriptases, such as, for example, the Superscript II reverse transcriptase (shown herein as prod-dnd, SEQ ID NO: 2). The improved thermal stability allows for reverse transcription of RNA to cDNA at temperatures above 37° C., thereby reducing error rates introduced during cDNA synthesis. As a result, the reverse transcriptases of the invention allow for increased accuracy in transcriptomics.

Reverse transcriptases of the invention may comprise a polypeptide comprising a sequence of amino acids having at least about 95% sequence identity with the reverse transcriptase of SEQ ID NO: 2, and at least one amino acid substitution at an amino acid position selected from positions 56, 72, 138, 163, 232, 234, 249, 290, 344, 420, 424, 444, and 615.

The at least one amino acid substitution may be selected from:

S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, Q;
V at position 444 substituted with G, A, L, or I; and
D at position 615 substituted with E, N, or Q.

For example, at least one amino acid substitution may be S56A, G138S, S232T, L234E, G290K, Y344F, T420V, G424D, V444I, and D615E. In addition, any of the following are examples of mutations according to the invention: S27T, V43K, A46P, L48I, A54P, S56A, S60W, Q68K, L72Q/R, E123Q, Y133C, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, Q562E, D583N, K550S, D615E, A619E, F625W/H, R629K, H642D, and K658E.

A reverse transcriptase of the invention further comprises at least one additional amino acid substitution at an amino acid position selected from positions 524, 583, and 562. The additional amino acid substitution may be selected from:

D at position 524 substituted with G, A V, L, or I;
D at position 583 substituted with E, N, or Q; and
E at position 562 substituted with D, N, or Q.

For example, the at least one additional amino acid substitution may be selected from D524G, D583N, and E562Q.

In some embodiments, a reverse transcriptase comprises any number of substitutions from among positions 56, 138, 234, 290, 344, 420, 424, 444, 615, 524, 583, and 562. For example, the reverse transcriptase may comprise substitutions in at least 3 amino acid positions selected from positions 56, 138, 234, 290, 344, 420, 424, 444, 615, 524, 583, and 562. The reverse transcriptase may comprise substitutions in at least 5 amino acid positions selected from positions 56, 138, 234, 290, 344, 420, 424, 444, 615, 524, 583, and 562. The reverse transcriptase may comprise substitutions in at least 10 amino acid positions selected from positions 56, 138, 234, 290, 344, 420, 424, 444, 615, 524, 583, and 562. The reverse transcriptase may comprise substitutions in 12 amino acid positions selected from positions 56, 138, 234, 290, 344, 420, 424, 444, 615, 524, 583, 562.

In aspects of the invention, reverse transcriptases of the invention comprise a polypeptide comprising a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, 615, and 642.

The at least one amino acid substitution is selected from:

S at position 56 substituted with G, A, V, L, or I;
G at position 138 substituted with S, C, T, or M;
S at position 232 substituted with C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q; and
H at position 642 substituted with D, E, N, or Q.

For example, the at least one amino acid substitution may be selected from S56A, G138S, S232T, L234E, G290K, Y344F, T420V, G424D, V444I, D615E, and H642D.

The reverse transcriptase may further comprise at least one additional amino acid substitution at an amino acid position selected from positions 524, 583, 562, 204, and 306.

The at least one additional amino acid substitution may be selected from:

D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

For example, the additional amino acid substitution may be G524D, N583D, Q562E, R204H, or K306T.

Reverse transcriptase of the present invention exhibit increased thermal stability relative to both wild type reverse transcriptases as well as common commercial reverse transcriptases, such as Superscript II (SEQ ID NO: 2). For example, reverse transcriptases of the invention at 50° C. have at least about 50% of the reverse transcription activity of either the wild type reverse transcriptase or the reverse transcriptase of SEQ ID NO: 2 at 42° C. However, depending on the number of mutations and conditions, at 50° C. or greater the activity of a reverse transcriptase of the invention may even exceed about 90% of the reverse transcription activity of either the wild type reverse transcriptase or the reverse transcriptase of SEQ ID NO: 2 at 42° C. For example, when 10 or more mutations are present, the reverse transcription activity exceeds 80% of the reverse transcription activity of the reverse transcriptase of SEQ ID NO: 2 at 42° C.

Further the activity of reverse transcriptases of the invention exceeds physiological activity of, for example, a reverse transcriptase as shown in SEQ ID NO: 2, at even higher temperatures, for example, 65° C. For example, a reverse transcriptase of the invention at temperatures of about 65° C. or greater shows at least 50% of the reverse transcription activity of the reverse transcriptase of SEQ ID NO: 2 at 42° C. In contrast, the reverse transcriptase activity of either a wild type transcriptase or that shown in SEQ ID NO: 2 would be considerably inhibited at temperatures above about 50° C. and nearly inactive at temperatures approaching about 65° C. Again, however, depending on the number of mutations and conditions, at about 65° C. or greater the reverse transcription activity of a reverse transcriptase of the invention may even exceed 80% of the reverse transcription activity of either the reverse transcriptase shown in SEQ ID NO: 2 or the wild type reverse transcriptase at 42° C. For example, when 10 or more mutations are present, the reverse transcription activity may exceed 70% of the reverse transcription activity of either the wild type reverse transcriptase or the reverse transcriptase shown in SEQ ID NO: 2 at 42° C.

Reverse transcriptases of the invention have improved activity compared to conventional commercial reverse transcriptases, including wild type reverse transcriptase, in the presence of inhibitors. Various inhibitors are found in a variety of samples that cause wild type and commercially-available reverse transcriptases to perform inefficiently. For example, plant samples typically contain polysaccharides, phenolics, and flavonoids that inhibit reverse transcription. Sample preparation steps also frequently introduce reverse transcription inhibitors, for example detergents, alcohols, salts, heparin, and hematin.

The present invention further provides methods of reverse transcribing cDNA from RNA using a reverse transcriptase of the invention.

Preferred methods of the invention comprise the steps of providing to a sample comprising RNA a reverse transcriptase comprising a polypeptide comprising a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, and 615; and reagents for reverse transcription. The methods further comprise the step of performing a reverse transcription reaction between the reverse transcriptase and the RNA in the sample to form cDNA.

The at least one amino acid substitution may be selected from:

S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I; and
D at position 615 substituted with E, N, or Q.

For example, the at least the at least one amino acid substitution may be S56A, G138S, S232T, L234E, G290K, Y344F, T420V, G424D, V444I, and D615.

The reverse transcriptase may further comprise at least one additional amino acid substitution at an amino acid position selected from positions 524, 583, and 562. The at least one additional amino acid substitution may be selected from:

D at position 524 substituted with G, A V, L, or I;
D at position 583 substituted with E, N, or Q; and
E at position 562 substituted with D, N, or Q.

In one example, the additional amino acid substitution is selected from G524D, N583d, and Q562E.

The reverse transcriptase may comprise any number of substitutions from among positions 56, 138, 234, 290, 344, 420, 424, 444, 615, 524, 583, and 562. For example, the reverse transcriptase may comprise substitutions in at least 3 amino acid positions selected from positions 56, 138, 234, 290, 344, 420, 424, 444, 615, 524, 583, and 562. The reverse transcriptase may comprise substitutions in at least 5 amino acid positions selected from positions 56, 138, 234, 290, 344, 420, 424, 444, 615, 524, 583, and 562. The reverse transcriptase may comprise substitutions in at least 10 amino acid positions selected from positions 56, 138, 234, 290, 344, 420, 424, 444, 615, 524, 583, and 562. The reverse transcriptase may comprise substitutions in 13 amino acid positions selected from positions 56, 138, 234, 290, 344, 420, 424, 444, 615, 524, 583, 562.

In aspects of the invention, reverse transcriptases of the invention comprise a sequence of amino acids having at least about 95% sequence identity with the reverse transcriptase of SEQ ID NO: 2, and at least one amino acid substitution at an amino acid position selected from positions 56, 138, 234, 290, 344, 420, 424, 444, 615. 444, 615, and 642.

The at least one amino acid substitution is selected from:

S at position 56 substituted with G, A, V, L, or I;
G at position 138 substituted with S, C, T, or M;
S at position 232 substituted with C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q; and
H at position 642 substituted with D, E, N, or Q.

For example, the amino acid substitution may be selected from S56A, G138S, S232T, L234E, G290K, Y344F, T420V, G424D, V444I, D615E, and H642D.

The reverse transcriptase may further comprise at least one additional amino acid substitution at an amino acid position selected from positions 524, 583, 562, 204, and 306.

The additional amino acid substitution may also be selected from:

D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

In one alternative, the additional amino acid substitution is selected from G524D, N583D, Q562E, R204H, and K306T.

Use of reverse transcriptases of the invention allows reactions to occur at a temperature of 50° C. or greater without the loss of enzyme activity that would occur with conventional reverse transcriptases. Accordingly, the performing step may be conducted at a temperature of about 65° C. or greater with an activity of at least about 50% of the activity of the reverse transcriptase shown in SEQ ID NO: 2 at 42° C. Due to the increased thermostability of the reverse transcriptases of the invention, the increased reaction temperature allows for both highly active reverse transcriptase activity and reduced nucleotide base addition errors in cDNA synthesis. Moreover, the reverse transcription reaction may result in a reduced incubation time, for example the incubation time may be about 5, 10, 15, 20, or 30 minutes, in comparison to typical methods requiring 50 minutes.

Aspects of the invention provide modified reverse transcriptases comprising at least one mutation in at least one domain of the reverse transcriptase of SEQ ID NO: 2. Importantly, the modified reverse transcriptases of the invention exhibit increased thermal stability relative to either the wild type reverse transcriptase or that shown in SEQ ID NO: 2 such that the activity of the reverse transcriptase at temperatures of about 50° C. or greater is at least about 90% of the activity of the transcriptase of SEQ ID NO: 2 at 42° C.

Preferred mutations include an amino acid substitution at position 27, 138, 200, 204, 212, 218, 231, 232, 234, 237, 242, 249, 264, 265, 267, and/or 272 in the palm domain of SEQ ID NO: 2. In addition, the invention contemplates mutations at positions 43, 46, 48, 54, 56, 72, 163, and/or 177 in the finger domain of the; positions 280, 281, 290, 306, 335, 338, 339, 344, 345, 346, and/or 349 in the thumb domain; positions 376, 413, 420, 424, 443, and/or 444 in the connection domain, and/or positions 518, 524, 528, 550, 554, 562, 583, 615, 619, 625, 629, 642, and/or 658 in the RNAse H domain of SEQ ID NO: 2.

Below is a list of preferred substitution mutation for use in the invention:

S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

A modified reverse transcriptase of the invention may have substitutions in one to 14 amino acid positions selected from positions 56, 72, 138, 204, 232, 234, 290, 306, 344, 420, 424, 444, 524, 562, 583, 615, and 642.

In addition, preferred amino acid substitutions include S56A, G138S, S232T, L234E, G290K, Y344F, T420V, G424D, V444I, and/or D615E. In addition to the foregoing, an additional amino acid substitution selected from G524d, N583D, and Q562E may be added. In other embodiments, the amino acid substitution is selected from L72Q, T163K, N249E, and H642D. In still other embodiments, the amino acid substitution is selected from S56A, G138S, S232T, L234E, G290K, Y344F, T420V, G424D, V444I, D615E, and H642D. That embodiment may also include at least one additional amino acid substitution selected from D524G, D583N, E562Q, H204R, and T306K.

In specific embodiments, the amino acid substitutions is selected from S27T, V43K, A46P, L48I, A54P, S56A, L72Q, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, E562Q, D583N, K550S, D615E, A619E, F625W/H, R629K, H642D, and K658E with respect to SEQ ID NO: 2.

In preferred embodiments, a modified reverse transcriptase of the invention demonstrates enzymatic activity at temperatures of about 65° C. or greater that is equivalent to at least about 50% of the reverse transcription activity of the reverse transcriptase shown in SEQ ID NO: 2 at about 42° C. The activity of a reverse transcriptase of the invention is improved in the presence of inhibitors. Additionally, modified reverse transcriptases of the invention exhibit increased thermal stability relative to a reverse transcriptase of SEQ ID NO: 2 and may include at least one amino acid substitution selected from the group consisting of E5K; M39V or M39L; 149V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

Specifically, activity of a reverse transcriptase of the invention is improved in the presence of inhibitors relative to a reverse transcriptase shown in SEQ ID NO: 2 and may include at least one amino acid substitution selected from the group consisting of M39V or M39L; 149V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In other embodiments, a reverse transcriptase of the invention exhibits improved activity in formalin-fixed samples relative to a reverse transcriptase of SEQ ID NO: 2 and may include at least one amino acid substitution selected from the group consisting of M39V or M39L; 149V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In still other embodiments, a reverse transcriptase of the invention exhibits increased thermal stability relative to a reverse transcriptase of SEQ ID NO: 2 and may include at least one amino acid substitution selected from the group consisting of A32V, E286R, E302K, W388R, and L435R.

Activity of reverse transcriptases of the invention in the presence of inhibitors is also improved relative to the reverse transcriptase of SEQ ID NO: 2 and may include at least one amino acid substitution selected from the group consisting of A32V, E286R, E302K, W388R, and L435R. Likewise, the reverse transcription activity of reverse transcriptases of the invention is improved in formalin-fixed samples relative to a reverse transcriptase of SEQ ID NO: 2 and may include at least one amino acid substitution selected from the group consisting of A32V, E286R, E302K, W388R, and L435R.

In certain embodiments, modified reverse transcriptases of the invention have at least about 95% sequence identity with respect to the reverse transcriptase shown in SEQ ID NO: 2.

Aspects of the invention include methods of reverse transcribing cDNA from RNA. Such methods include utilizing a modified reverse transcriptase as provided herein. Such modified enzymes exhibit improved thermal stability relative to existing reverse transcriptase such that their activity at temperatures of about 50° C. or greater is at least about 90% of the reverse transcription activity of conventional reverse transcriptases at 42° C. and providing to the sample reagents for reverse transcription, and performing a reverse transcription reaction between the reverse transcriptase and the RNA in the sample. The reverse transcription reaction is conducted at a temperature of 50° C. or greater to form the cDNA.

Modified enzymes of the invention comprise at least one amino acid substitution at a position selected from positions 27, 138, 200, 204, 212, 218, 231, 232, 234, 237, 242, 249, 264, 265, 267, and 272 in a palm domain of the reverse transcriptase shown in SEQ ID NO: 2, positions 43, 46, 48, 54, 56, 72, 163, and 177 in a finger domain of SEQ ID NO: 2, positions 280, 281, 290, 306, 335, 338, 339, 344, 345, 346, and 349 in a thumb domain of SEQ ID NO: 2, positions 376, 413, 420, 424, 443, and 444 in a connection domain of SEQ ID NO: 2, and positions 518, 524, 528, 550, 554, 562, 583, 615, 619, 625, 629, 642, and 658 in the RNAse H domain of the reverse transcriptase shown in SEQ ID NO: 2.

For example, the amino acid substitution may be selected from:

S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

Modified reverse transcriptases of the invention may comprise substitutions in at least 3 amino acid positions up to at least 12 amino acid positions, wherein the amino acid positions are selected from positions 56, 72, 138, 204, 232, 234, 290, 306, 344, 420, 424, 444, 524, 562, 583, 615, and 642. Specifically, the amino acid substitution may be selected from S56A, G138S, S232T, L234E, G290K, Y344F, T420V, G424D, V444I, and D615E. In certain embodiments, the modified reverse transcriptases may comprise at least one additional amino acid substitution selected from G524D, N58$^{3}$D, and Q562E. The at least one amino acid substitution may be selected from L72Q, T163K, N249E, and H642D. Additionally and/or alternatively, the amino acid substitution is selected from S56A, G138S, S232T, L234E, G290K, Y344F, T420V, G424D, V444I, D615E, and H642D. This embodiment may further comprise additional amino acid substitution selected from D524G, D583N, E562Q, H204R, and T306K.

Methods of the invention may further comprise any known reagents and methods for reverse transcription. For example, the providing step may comprise providing to the sample capture oligos that capture target RNA molecules.

BRIEF DESCRIPTION OF THE DRAWINGS

FIG. 1B gives efficiency scores for the enzymes.

FIG. 3D shows a table of results for the thermal ramp assay of FIG. 3C.

DETAILED DESCRIPTION

Figure 1A:
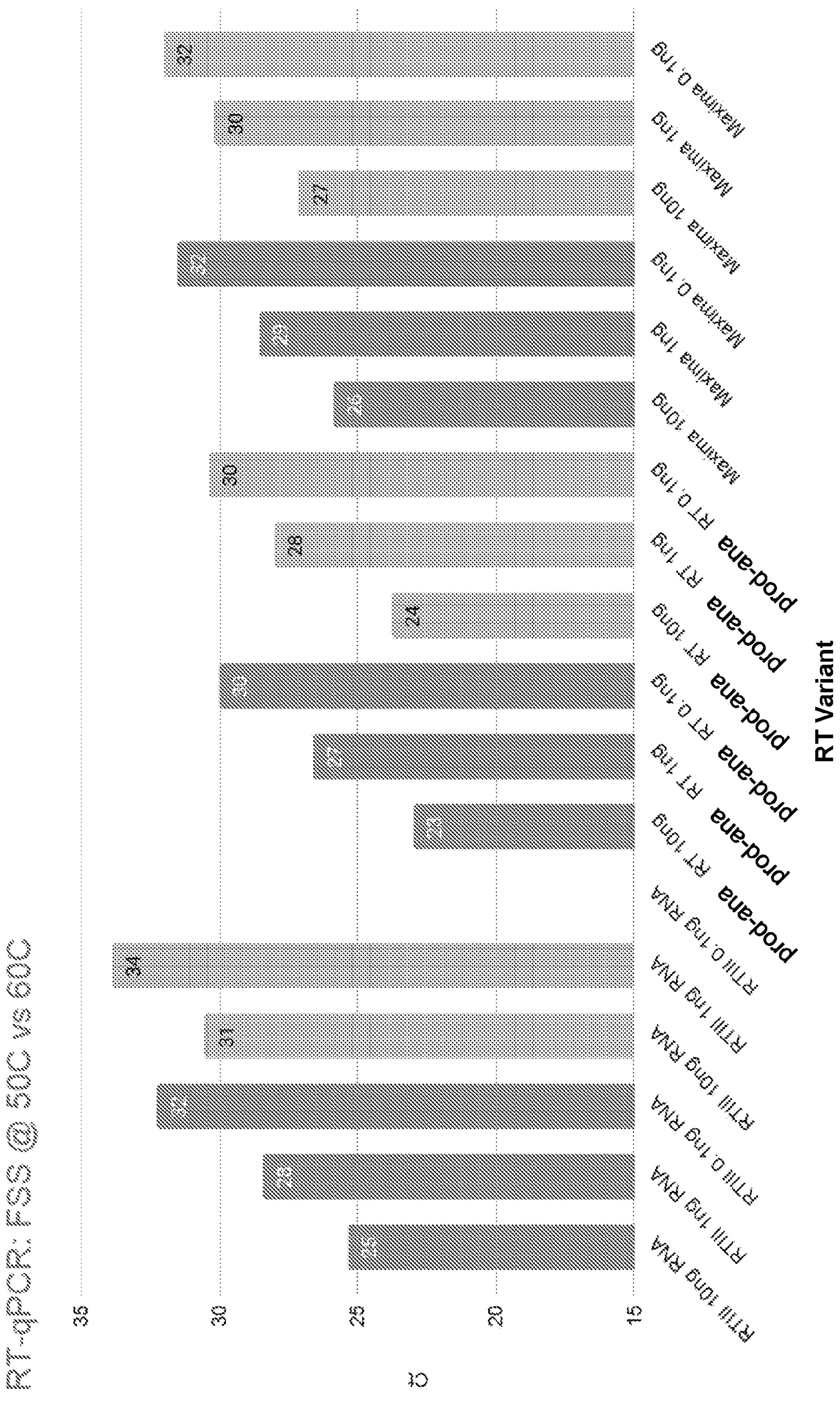
FIG. 1A gives qPCR results showing thermo-activity of RT enzymes of the disclosure.

The present invention provides reverse transcriptase enzymes with increased thermal stability as compared to conventional reverse transcriptases, such as Superscript II (SEQ ID NO: 2) or the wild type reverse transcriptase shown in SEQ ID NO: 1. The improved thermal stability allows for reverse transcription of RNA to cDNA at temperatures above about 42° C., thereby reducing error rates introduced during cDNA synthesis. As a result, the reverse transcriptases of the invention allow for increased accuracy in the determination of transcriptomes of living organisms.

Specifically, disclosed are modified reverse transcriptases that comprise substitutions at least one position in SEQ ID NO: 2 selected from positions 56, 72, 138, 163, 234, 249, 290, 344, 420, 424, 444, 615, 642, 524, 583, 562, 204, and 306. For example, the amino acid substitutions may be:

S at position 56 substituted with G, A, V, L, or I;
G at position 138 substituted with S, C, T, or M;
S at position 232 substituted with C, T, or M;
L at position 234 substituted with D, E, N, or Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q;
H at position 642 substituted with D, E, N, or Q.
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

The invention recognizes that increased temperatures during reverse transcription reactions reduces non-target primer binding, error rates in cDNA synthesis and reduces RNA secondary structures. Accordingly, the improved thermal stability of the reverse transcriptases of the invention allows for reverse transcription of RNA to cDNA at temperatures above 37° C., the optimal temperature for wild type and other conventional reverse transcriptases. By allowing for an increased reaction temperature, reverse transcriptases of the invention result in reduced error rates in cDNA synthesis.

Moreover, the reverse transcriptases of the present invention provide additional advantages over wild type and other conventional reverse transcriptases, including improved efficiency in the presence of inhibitors or reverse transcriptase and improved efficiency in formalin-fixed samples.

Reverse Transcription

Reverse transcription is the synthesis of DNA from an RNA template and produces cDNA. Reverse transcriptases use an RNA template and a short primer complementary to the 3' end of the RNA to direct the synthesis of the first strand cDNA, which can be used directly as a template for the Polymerase Chain Reaction (PCR). This combination of reverse transcription and PCR allows the detection of RNA in a sample and production of the corresponding cDNA. RNase H activity, from either the reverse transcriptase or supplied exogenously, may be used to separate RNA/cDNA hybrids. Further components may also include buffers, one or more primers, a dNTP Mix (a mix of the nucleotides dATP, dCTP, dGTP and dTTP), agents needed for PCR, synthesis of a second DNA strand, or amplification reagents.

Reverse transcription may be performed by capture oligos that have a free, 3' poly-T region. The 3' portions of the capture oligos may include target-specific sequences or oligomers, for example capture primers to reverse transcribe RNA molecules comprising the capture sequence. The oligomers may be random or “not-so-random” (NSR) oligomers (NSROs), such as random hexamers or NSR hexamers. The oligos may include one or more handles such as primer binding sequences cognate to PCR primers that are used in the amplifying step or the sequences of NGS sequencing adaptors. The reverse transcription primers may include template switching oligos (TSOs), which may include poly-G sequences that hybridize to and capture poly-C segments added during reverse transcription.

Reverse transcription of RNA may comprise use of a capture sequence and a capture primer or probe. Primer sequences may comprise a binding site, for example a primer sequence that would be expected to hybridize to a complementary sequence in a nucleic acid molecule. The primer sequence may also be a “universal” primer sequence, i.e. a sequence that is complementary to nucleotide sequences that are very common for a particular set of nucleic acid fragments. Primer sequences may be P5 and P7 primers as provided by Illumina, Inc., San Diego, California. The primer sequence may also allow a capture probe to bind to a solid support, such as a template particle.

This process may comprise hybridizing the reverse transcription primer to the probe followed by a reverse transcription reaction. The complement of a nucleic acid when aligned need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Reverse transcription can also be used to add a barcode, a unique molecular identifier (UMI), sequencing adaptors, or any additional sequences of nucleotides to the final cDNA product. For example, the reverse transcription primer may include additional bases that add the barcode or UMI to cDNA product.

A barcode is any sequence of nucleotides which may be used to derive information regarding the nucleic acid product, for example after sequencing. For example, the same sample barcode may be attached to each nucleic acid from a single sample source. The sample barcode may then be used to differentiate nucleic acids derived from different samples after sequencing the nucleic acids and the sample barcode.

UMIs are a type of barcode that may be provided to a sample to make each nucleic acid molecule, together with its barcode, unique, or nearly unique. This may be accomplished by adding one or more UMIs to one or more capture probes of the present invention. By selecting an appropriate number of UMIs, every nucleic acid molecule in the sample, together with its UMI, will be unique or nearly unique.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, "Counting Molecules in cell-free DNA and single cells RNA", Karolinska Institute, Stockholm Sweden, incorporated herein by reference.

For example, in the context of RNA analysis, it may be advantageous to analyze the relative or absolute amounts of each RNA molecule in a sample, for example a single-cell sample. Typical methods of RNA analysis, however, first require reverse transcription of the RNA molecules into cDNA copies, followed by amplification of the cDNA molecules. The cDNA molecules must then be amplified in order to create sufficient nucleic acids to be analyzed. As a result, the absolute number of each original RNA molecule present in the sample is lost, with multiple copies of each molecule now present in the prepped sample to be analyzed. Moreover, due to amplification bias that results in the non-uniform amplification of some cDNA molecules at a greater degree than other cDNA molecules, information regarding the relative amounts of each RNA molecule in the original sample is also lost. By providing a UMI to each cDNA molecule prior to amplification, each cDNA molecule (corresponding to each RNA molecule in the sample) is made unique or nearly unique. After amplifying each cDNA molecule (together with its UMI), the amplified cDNA molecules can then be sequenced, and sequence reads generated for each molecule. Sequence reads having both the same base sequence and UMI can be collapsed into a single sequence read and considered a read from a single RNA molecule in the original sample. Sequence reads having the same base sequence but different UMIs are not collapsed, and each sequence read is considered a separate instance of the RNA molecule present in the original sample.

After reverse transcription, biotinylated capture baits or probes may also be used for the targeted enrichment of specific cDNA molecules of interest. Biotinylated capture probes may comprise RNA, DNA, or a hybrid of RNA and DNA nucleotides. The biotinylated RNA capture probes may be added to the cDNA library and incubated for a period of time and at a temperature sufficient for the biotinylated RNA capture probes to hybridize to their target molecules of cDNA based on Watson-Crick base pairing. For example, the mixture containing cDNA and probes may be incubated at 65 degrees Celsius for 24 hours. After hybridization, the biotinylated RNA capture probes that are hybridized with the target cDNA molecules may be captured and segregated using streptavidin or an antibody. The target cDNA molecules can then be amplified and sequenced.

Any known sequencing technology may be used to analyze cDNA reverse transcribed by reverse transcriptases and methods of the invention. An example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured, and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference. For example, an Illumina Mi-Seq sequencer may be used to generate a plurality of sequence reads that may be uploaded to a web portal for analysis by, for example, the Genome Analysis Toolkit (GATK) and/or analyzed using methods shown in U.S. Pat. No. 8,209,130, incorporated by reference.

Analyzing the sequence reads may be performed using known software and following a multistep procedure known in the art. For example, first, the quality of each sequence read, i.e., FASTQ sequence, may be assessed using the software FASTQC. Next, the reads may be trimmed by, for example, Trimmomatic software. The trimmed sequence reads may then be mapped to a human genome using the HISAT2 software. HISAT2 output files in a SAM (sequence alignment/map format), which may be compressed to binary sequence alignment/map files using SAMtools version prior sequence read quantification. Afterward, mapped reads may be counted using the feature Counts software.

Reverse Transcriptases

As discussed above, a reverse transcriptase is an enzyme used to generate cDNA from an RNA template, a process termed reverse transcription. It is mainly associated with retroviruses. However, some non-retroviruses also use reverse transcriptase. Retroviral reverse transcription has three sequential biochemical activities: RNA-dependent DNA polymerase activity, ribonuclease H, and DNA-dependent DNA polymerase activity. These activities are used by the retrovirus to convert single-stranded genomic RNA into double-stranded cDNA. The same sequence of reactions is used in the laboratory to convert RNA to cDNA for use in molecular cloning, RNA sequencing, polymerase chain reaction, or genome analysis.

Reverse transcriptases are members of a specific enzymatic family included in the DNA polymerase superfamily. Enzymes of this superfamily, despite a relatively low amino acid sequence homology and distinct origin, share a similar 3D structure, where DNA polymerase consists of 3 separate domains: palm, thumb, and fingers. In addition, reverse transcriptases with RNAse H activity reveal the unique RNAse H domain with a respective active site and connection domain.

The Moloney murine leukemia virus (MMLV) is a retrovirus known to cause cancer in mice, and its associated reverse transcriptase may be used in the laboratory to convert RNA to cDNA. The MMLV wild type reverse transcriptase is a 75-kDa monomer that has optimal activity at 37° C. (approximately the median body temperature of a mouse or a human). The MMLV reverse transcriptase comprises domains referred to as fingers, palm, thumb, connection, and RNase H domains. The active site of the DNA polymerase reaction resides in the fingers/palm/thumb domain, while that of RNase H reaction lies in the RNase H domain.

Fingers (41-124, 160-192 a.a.), palm (1-40, 125-159, 193-275 a.a.), and thumb (276-361) domains comprise the N-terminal of MMLV RT, while connection domain (362-496 a.a.) and RNAse H (497-671 a.a.) are located at the C-terminal part. Fingers domain has been proposed to provide an intermediate binding site for template-primer in between phosphonucleotidyl transfer reactions. The thumb domain plays a crucial role in substrate binding and processivity. In the palm domain, regions I125-F155, L220-E233, and K257-E275 are located on the surface, interacting with a template. The connection domain comprises P360-K373, Y394-A436, and S453-A462 on the surface, which interacts with a template, and five consecutive hydrophobic residues L432-V433-I434-L435-A436. RNAse H domain can change its conformation and is believed to participate in the processive DNA synthesis.

The Superscript II reverse transcriptase (ThermoFisher) is a mutant MMLV reverse transcriptase that has reduced RNase H activity and increased thermal stability as compared to the wild type MMLV reverse transcriptase. The Superscript II reverse transcriptase is a commonly-used commercial form of the enzyme and is the primary basis below for comparison of reverse transcriptases of the invention. The sequence of the Superscript II reverse transcriptase is shown in SEQ ID NO: 2.

A reverse transcriptase of the invention has at least one amino acid substitution as compared to the reverse transcriptase of SEQ ID NO: 2.

Modified reverse transcriptases of the invention have increased thermal stability with respect to both the wild type version and the Superscript II version of the enzyme. Increased thermal stability of one reverse transcriptase relative to another reverse transcriptase means that the reverse transcriptase with increased thermal stability is less prone to loss of activity at elevated temperatures, for example, above 37° C. Increased stability of an enzyme also may include avoidance of denaturation mechanisms in order to realize their full potential as catalysts. Moreover, for cDNA synthesis, a higher reaction temperature is desirable because it reduces RNA secondary structures and nonspecific primer binding. Stability between two enzymes can be determined by comparing the remaining activity of both enzymes after exposure to a particular condition (for example, elevated temperature, in the presence of inhibitors of that enzyme, or in fixed samples). Alternatively, the stability may be determined by comparing the remaining or residual acidity of the enzyme after incubation at a given condition (for example time or temperature) as compared to the initial activity before incubation.

Increased efficiency of one reverse transcriptase relative to another reverse transcriptase means that under a set of conditions, the more efficient enzyme results in fewer base calling errors over time.

Increased activity of one enzyme relative to another enzyme means that the enzyme with increased activity converts the substrate at a higher rate—with regard to reverse transcription, this means the rate at which RNA (the substrate) is used to synthesize cDNA. The SI unit for enzyme activity is katal (1 katal=1 mol $s^{-1}$). A more practical and commonly used value is enzyme unit (U)=1 μmol $min^{-1}$. 1 U corresponds to 16.67 nanokatals and is defined as the amount of the enzyme that catalyzes the conversion of 1 micro mole of substrate per minute. The specific activity of an enzyme is the activity of an enzyme per milligram of total protein (expressed in μmol $min^{-1}mg^{-1}$).

Reverse transcriptase activity may be determined in an assay measuring formation of cDNA over time. For example, a reverse transcriptase may be incubated with an RNA template, primers and a suitable dNTP mixture, and the production of cDNA or consumption of dNTP may be monitored.

Disclosed herein are reverse transcriptases that comprise amino acid substitutions of at least one amino acid substitution at an amino acid position selected from positions 56, 138, 234, 290, 344, 420, 424, 444, 615, 444, 615, 642, 524, 583, 562, 204, and 306 with respect to SEQ ID NO: 2. For example, the amino acid substitutions may be:

S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I;
D at position 615 substituted with E, N, or Q;
H at position 642 substituted with D, E, N, or Q.
D at position 524 substituted with G, A V, L, or I;
D at position 583 substituted with E, N, or Q;
E at position 562 substituted with D, N, or Q;
H at position 204 substituted with K or R; and
T at position 306 substituted with H, K, or R.

It is understood that the reverse transcriptases of the invention may comprise additional mutations that do not alter the function, i.e. increased thermostability, of the reverse transcriptase.

For example, the reverse transcriptase may comprise additional conservative mutations. Conservative amino acid substitutions are substitutions of an amino acid with a different amino acid having similar properties, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

In aspects of the invention, the reverse transcriptase does not comprise one or more of following mutations: E5K; M39V or M39L; 149V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; L671P, A32V, E286R, E302K, W388R, and L435R. For example, the reverse transcriptase comprises the wild type amino acid at the positions identified, or a conservative substitution at the wild type amino acid position.

A reverse transcriptase with at least X % sequence identity means that the enzyme has an amino acid sequence characterized in that, within a stretch of 100 amino acids, at least X amino acids residues are identical to the sequence of the corresponding sequence. Sequence identity may be determined by sequence alignment in the form of sequence comparison. Methods of sequence alignment are well known in the art and include various programs and alignment algorithms. The Basic Local Alignment Search Tool (BLAST) may also be used in connection with the sequence analysis programs blastp, blastn, blastx, tblastn and tblastx.

For example, because the wild type MMLV is 671 amino acids in length, the enzyme may tolerate a number of substitutions, for example conservative substitutions, without losing the reverse transcription properties of the enzyme. However, it is understood that mutations at certain positions relative to the wild type will reduce efficacy of the wild type enzyme, while other rarer substitutions may increase efficacy of the wild type enzyme. Accordingly, by the present invention, it has been discovered that amino acid substitutions at amino acid positions 56, 72, 138, 163, 234, 249, 290, 344, 420, 424, 444, 615, 444, 615, 642, 524, 583, 562, 204, and 306 may enhance the properties of the wild type enzyme. It is understood that an enzyme comprising substitutions at each of the 20 positions identified by present invention would have a 97.32% sequence identity with the wild type enzyme. Enzymes of the present invention may comprise additional substitutions that do not alter the properties of the present invention, for example an additional 15 amino acid substitutions, for example conservative substitutions. Accordingly, the enzyme of the present invention may have 95% sequence identity with the wild type MMLV enzyme. The same principles hold true for the Superscript II version.

Aspects of the invention provide modified reverse transcriptases comprising at least one mutation in at least one domain of the Moloney Murine Leukemia Virus (MMLV) reverse transcriptase of SEQ ID NO: 2. Importantly, modified reverse transcriptases of the invention exhibit increased thermal stability relative to the wild type reverse transcriptase such that at temperatures of about 50° C. or greater the activity is at least about 90% of the activity of the wild type reverse transcriptase at 42° C.

Preferred amino acid substitutions occur at positions 27, 138, 200, 204, 212, 218, 231, 232, 234, 237, 242, 249, 264, 265, 267, and/or 272 in a palm domain of the MMLV reverse transcriptase, positions 43, 46, 48, 54, 56, 72, 163, and/or 177 in a finger domain of the MMLV reverse transcriptase, positions 280, 281, 290, 306, 335, 338, 339, 344, 345, 346, and/or 349 in a thumb domain of the MMLV reverse transcriptase, positions 376, 413, 420, 424, 443, and 444 in a connection domain of the MMLV reverse transcriptase, and positions 518, 524, 528, 550, 554, 562, 583, 615, 619, 625, 629, 642, and/or 658 in the RNAse H domain of the MMLV reverse transcriptase.

Preferred substitutions are selected from:

S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

In addition, modified reverse transcriptases may have substitutions in at least one to at least 14 amino acid positions selected from positions 56, 72, 138, 204, 232, 234, 290, 306, 344, 420, 424, 444, 524, 562, 583, 615, and 642.

In some embodiments, the amino acid substitution is selected from S56A, G138S, S232T, L234E, G290K, Y344F, T420V, G424D, V444I, and D615E. The modified enzyme may comprise an additional substitution selected from G524D, N583D, and Q562E. In other embodiments, the amino acid substitution is selected from L72Q, T163K, N249E, and H642D. In still other embodiments, the amino acid substitution is selected from S56A, G138S, S232T, L234E, G290K, Y344F, T420V, G424D, V444I, D615E, and H642D. This embodiment may also include at least one additional amino acid substitution selected from D524G, D583N, E562Q, H204R, and T306K.

In specific embodiments, the amino acid substitutions may be selected from S27T, V43K, A46P, L48I, A54P, S56A, L72Q, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, E562Q, D583N, K550S, D615E, A619E, F625W/H, R629K, H642D, and K658E.

Modified reverse transcriptases of the invention generally have activity at temperatures of 65° C. or greater that is at least about 50% of the reverse transcription activity of the reverse transcriptase of SEQ ID NO: 2 at about 42° C. Preferably, the activity of the reverse transcriptase is improved compared to the reverse transcriptase of SEQ ID NO: 2 in the presence of inhibitors of reverse transcription. Additionally, modified reverse transcriptases of the invention exhibit increased thermal stability relative to, for example, a reverse transcriptase of SEQ ID NO: 2 and may include at least one amino acid substitution selected from the group consisting of E5K; M39V or M39L; 149V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

Samples and Sample Preparation

Any sample suspected of containing one or more nucleic acids that are to be detected or measured and quantified may be analyzed using the reverse transcriptases of the invention. For example, the sample may be a biopsy, a culture, or an environmental sample such as water or soil. Samples may be from a subject, such as an animal or human, they may be fluid, solid, a suspension, or tissue.

Examples of samples include cell or tissue cultures, blood, blood serum, blood plasma, needle aspirate, urine, semen, seminal fluid, seminal plasma, prostatic fluid, excreta, tears, saliva, sweat, biopsy, ascites, cerebrospinal fluid, pleural fluid, amniotic fluid, peritoneal fluid, interstitial fluid, sputum, milk, lymph, bronchial and other lavage samples, or tissue extract samples. The source of the sample may be solid tissue as from a fresh, frozen and/or preserved organ or tissue sample or biopsy or aspirate; or cells from any time in gestation or development of the subject. In a preferred embodiment of the method, the sample is selected from the group consisting of a body fluid, blood, blood plasma, blood serum, urine, bile, cerebrospinal fluid, a swab, a clinical specimen, an organ sample and a tissue sample, particularly a human, an animal or a plant, especially a human.

The sample may contain compounds which are naturally intermixed in nature as well as compounds not naturally intermixed with the sample in nature such as preservatives, anticoagulants, buffers, fixatives, nutrients, antibiotics, or the like.

Notably, many samples contain both natural and non-natural inhibitors of reverse transcriptases. For example, humic/fulvic acid, polysaccharides, phenolics, and flavonoids in plant samples inhibit reverse transcription activity. Additionally, proteins and fats from tissue samples, bile salts from stool samples, collagen from connective tissue samples, melanin and eumelanin in hair and skin samples, myoglobin from muscle tissue samples, complex polysaccharides in fecal samples, proteinases and calcium ions in milk and bone samples, and urea in urine samples all inhibit transcriptase activity. In addition, heme, hemoglobin, lactoferrin, and antibodies in blood samples all inhibit transcription activity.

Sample preparation steps also frequently introduce products that inhibit reverse transcriptases, for example EDTA, detergents/DDT, alcohols, salts, heparin, hematin, phenol: chloroform, proteases, nucleases, agarose, metal ions, and aldehydes all inhibit reverse transcription activity. Moreover, some artificial sample preparation products are introduced into a sample for the very purpose of removing unwanted natural products in the sample. For example, ethanols, proteinases, and phenol:chloroforms are typically used to wash samples of excess proteins, salts, and other natural products, and yet are themselves transcriptase inhibitors. Other sample preparation products are necessary for analysis of sample types. For example, detergents are frequently introduced to samples comprising cells in order to cause cell lysis and release nucleic acids to be analyzed. Detergents are also frequently used in methods of single cell sequences, for example droplet sequencing, to separate and compartmentalize individual cells for sequencing.

As a consequence, samples are typically washed of unwanted products or no-longer needed reagents multiple times during sample preparation. However, each washing results in the loss of at least some of the original sample and risks the introduction of contaminants.

Sample preservation steps may also result in the introduction of reverse transcriptase inhibitors. For example, Formalin-Fixed Paraffin-Embedded (FFPE) tissue preservation methods are a form of preservation and preparation for biopsy specimens. The tissue sample is first preserved by fixing it in formaldehyde to preserve the proteins and vital structures within the tissue. Next, it is embedded in a paraffin wax block, which allows for ease of cutting slices of required sizes to mount on a microscopic slide for examination. However, FFPE sample preparation also results in inhibition of reverse transcription activity.

Reverse transcriptases of the present invention exhibit improved reverse transcriptase activity in the presence of inhibitors of reverse transcriptase and preserved samples, for example FFPE samples, as compared to either the wild type MMLV enzyme or the reverse transcriptase shown in SEQ ID NO: 2. As a result, reverse transcriptases of the invention may be added directly to samples comprising an inhibitor without additional washing steps that result in the loss of the original sample or the introduction of contaminants. Additionally, reverse transcriptases of the invention may be added directly to preserved samples, for example fixed samples, also without the loss of reverse transcriptase activity.

Specifically, reverse transcriptases of the invention demonstrate improved activity in the presence of inhibitors of reverse transcription relative to the reverse transcriptase of SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In other embodiments, the activity of the reverse transcriptase is improved in formalin-fixed samples relative to the reverse transcriptase of SEQ ID NO: 2 and may include at least one amino acid substitution selected from the group consisting of M39V or M39L; I49V or I49T; M66L; Q91R or Q91L; P130S; L139P; I179T or I179V; D200N, D200A or D200G; Q221R; Q237R; T287A; A307V; T330P; L333Q; Y344H; A502V; D524A; L528I; H594R, H594K or H594Q; L603W or L603M; E607K, E607G or E607A; H634Y; A644V or A644T; N649S; D653G, D653A, D653H or D653V; K658R or K658Q; and L671P.

In still other embodiments, a reverse transcriptase of the invention exhibits increased thermal stability relative to the reverse transcriptase of SEQ ID NO: 2 and may include at least one amino acid substitution selected from the group consisting of A32V, E286R, E302K, W388R, and L435R.

The activity of reverse transcriptases of the invention is also improved in the presence of inhibitors of reverse transcription relative to the reverse transcriptase of SEQ ID NO: 2 and may include at least one amino acid substitution selected from the group consisting of A32V, E286R, E302K, W388R, and L435R. Likewise, the activity of reverse transcriptases of the invention is improved for formalin-fixed samples relative to the reverse transcriptase of SEQ ID NO: 2 and may include at least one amino acid substitution selected from the group consisting of A32V, E286R, E302K, W388R, and L435R.

Preferred reverse transcriptases of the invention comprise a at least about 95% sequence identity with respect to the reverse transcriptase of SEQ ID NO: 2.

Aspects of the invention include methods of reverse transcribing cDNA from RNA. Preferred methods include providing to a sample comprising RNA a modified reverse transcriptase of the invention comprising at least one mutation in at least one domain of the reverse transcriptase of SEQ ID NO: 2, wherein the modified reverse transcriptase exhibits an increased thermal stability relative to the thereto, such that an activity of the reverse transcriptase at temperatures of about 50° C. or greater is at least about 90% of the activity of the reverse transcriptase of SEQ ID NO: 2 at 37° C., and providing to the sample reagents for reverse transcription, and performing a reverse transcription reaction between the reverse transcriptase and the RNA in the sample. The reverse transcription reaction is conducted at a temperature of 50° C. or greater to form the cDNA.

In certain embodiments, the mutation comprises an amino acid substitution at a position selected from positions 27, 138, 200, 204, 212, 218, 231, 232, 234, 237, 242, 249, 264, 265, 267, and 272 in a palm domain of the reverse transcriptase, positions 43, 46, 48, 54, 56, 72, 163, and 177 in a finger domain of the reverse transcriptase, positions 280, 281, 290, 306, 335, 338, 339, 344, 345, 346, and 349 in a thumb domain of the reverse transcriptase, positions 376, 413, 420, 424, 443, and 444 in a connection domain of the reverse transcriptase, and positions 518, 524, 528, 550, 554, 562, 583, 615, 619, 625, 629, 642, and 658 in the RNAse H domain of the reverse transcriptase.

For example, the amino acid substitution may be selected from:

S at position 56 substituted with G, A, V, L, or I;
L at position 72 substituted with Q or R;
G at position 138 substituted with S, C, T, or M;
H at position 204 substituted with K or R;
S at position 232 substituted with C, T, or M;
L at position 234 substituted with D, E, N, Q;
G at position 290 substituted with H, K, or R;
T at position 306 substituted with H, K, or R
Y at position 344 substituted with F or M;
T at position 420 substituted with G, A, V, L, or I;
G at position 424 substituted with D, E, N, or Q;
V at position 444 substituted with G, A, L, or I;
D at position 524 substituted with G, A V, L, or I;
E at position 562 substituted with D, N, or Q;
D at position 583 substituted with E, N, or Q;
D at position 615 substituted with E, N, or Q; and
H at position 642 substituted with D, E, N, or Q.

The modified reverse transcriptases may comprise substitutions in at least 3 amino acid positions and up to at least 12 amino acid positions, wherein the amino acid positions are selected from positions 56, 72, 138, 204, 232, 234, 290, 306, 344, 420, 424, 444, 524, 562, 583, 615, and 642. Specifically, the at least one amino acid substitution may be selected from S56A, G138S, S232T, L234E, G290K, Y344F, T420V, G424D, V444I, and D615E. In certain embodiments, the modified reverse transcriptases comprise at least one additional amino acid substitution selected from G524D, N583D, and Q562E. The amino acid substitution is selected from L72Q, T163K, N249E, and H642D. Additionally and/or alternatively, the amino acid substitution is selected from S56A, G138S, S232T, L234E, G290K, Y344F, T420V, G424D, V444I, D615E, and H642D. This embodiment may further comprise at least one additional amino acid substitution selected from D524G, D583N, E562Q, H204R, and T306K.

Generally, the activity of the reverse transcriptases at temperatures of about 65° C. or greater is at least about 50% of the reverse transcription activity of the reverse transcriptase of SEQ ID NO: 2 at about 42° C.

Additionally, in methods of the invention, the sample comprising RNA may comprise one or more inhibitors of reverse transcription and the reverse transcription reaction may be more efficient than a reverse transcription reaction conducted using the reverse transcriptase of SEQ ID NO: 2 in the presence of the one or more. The sample comprising RNA may be formalin fixed, and the reverse transcription reaction may be more efficient than a reverse transcription reaction conducted with the reverse transcriptase of SEQ ID NO: 2 on a formalin-fixed sample.

In further embodiments, the performing step is conducted at a temperature of about 65° C. or greater and wherein the reverse transcription reaction is at least about 50% as active as a reverse transcription reaction conducted using the reverse transcriptase of SEQ ID NO: 2 at about 42° C.

Methods of the invention may further comprise any known reagents and methods for reverse transcription. For example, the providing step may comprise providing to the sample capture oligos that capture target RNA molecules.

EXAMPLES

Data are given characterizing RT enzymes of the disclosure.

FIG. 1A gives qPCR results showing that prod-ana RT has competitive thermo-activity with Maxima in RT-qPCR.

FIG. 1B gives efficiency scores for the enzymes.

First strand synthesis (FSS) was run at 50° C. and 60° C. using 10, 1, and 0.1 ng of total liver RNA as input with RT enzymes of the disclosure and Maxima followed by qPCR.

First strand synthesis (FSS) reactions were generated on ice by mixing 10 ng of total liver RNA, 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, and 200 U specified reverse transcriptase. FSS was run at various temperatures (42-65° C.) for 25 minutes followed by qPCR to assess cDNA yield. qPCR reactions were generated by mixing 1× SsoAdvanced Universal SYBR Green Supermix, 10% of the FSS reaction, and 0.6 uM of primers that anneal to the 5' end of the beta-actin gene.

The resulting cDNA values were assessed via Ct values as shown in FIG. 1. cDNA yields from prod-blh FSS are greater than 100-fold lower when FSS is incubated at 50° C. compared to 60° C. whereas prod-ana and Maxima are able to convert similar amounts of RNA to cDNA at 50° C. and 60° C. Prod-ana has competitive or better yields and efficiency than Maxima RNaseH minus reverse transcriptase at 50° C. and 60° C.

Figure 1C:
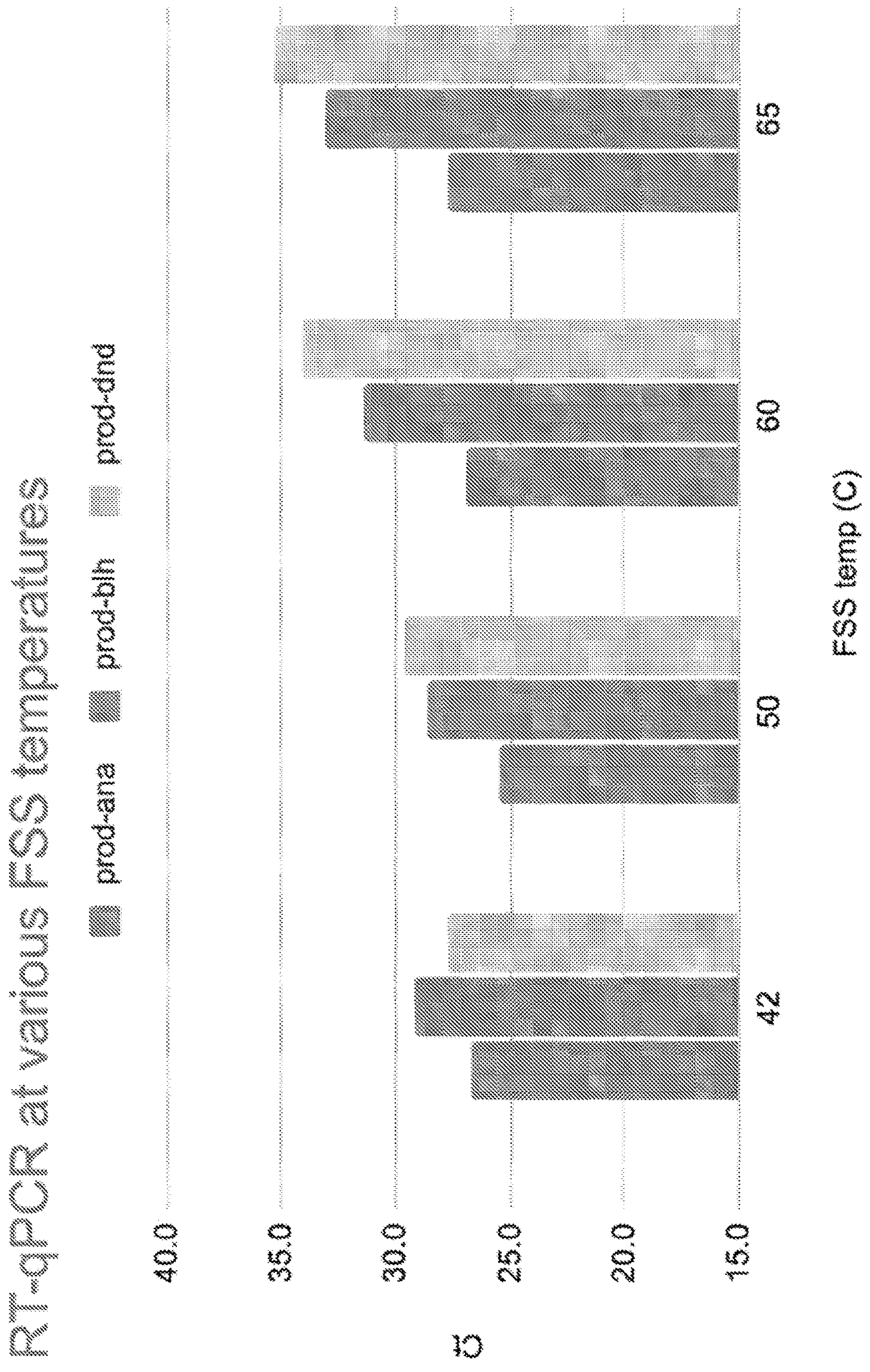
FIG. 1C shows RT-qPCR yields at elevated using RT enzymes of the disclosure.

FIG. 1C shows RT-qPCR yields at elevated using RT enzymes of the disclosure. First strand synthesis (FSS) reactions were generated on ice by mixing 10 ng of total liver RNA, 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, and 200 U specified reverse transcriptase. FSS was run at various temperatures (42-65° C.) for 25 minutes followed by qPCR to assess cDNA yield. qPCR reactions were generated by mixing 1× SsoAdvanced Universal SYBR Green Supermix, 10% of the FSS reaction, and 0.6 uM of a primers that anneal to the 5' end of a Beta-actin gene.

The resulting cDNA values were assessed via Ct values and are shown in FIG. 1C. Prod-blh had equivalent cDNA yield at 42° C. and 50° C. Prod-ana was the most thermostable variant and had equivalent yields at all temperatures tested.

Figure 2A:
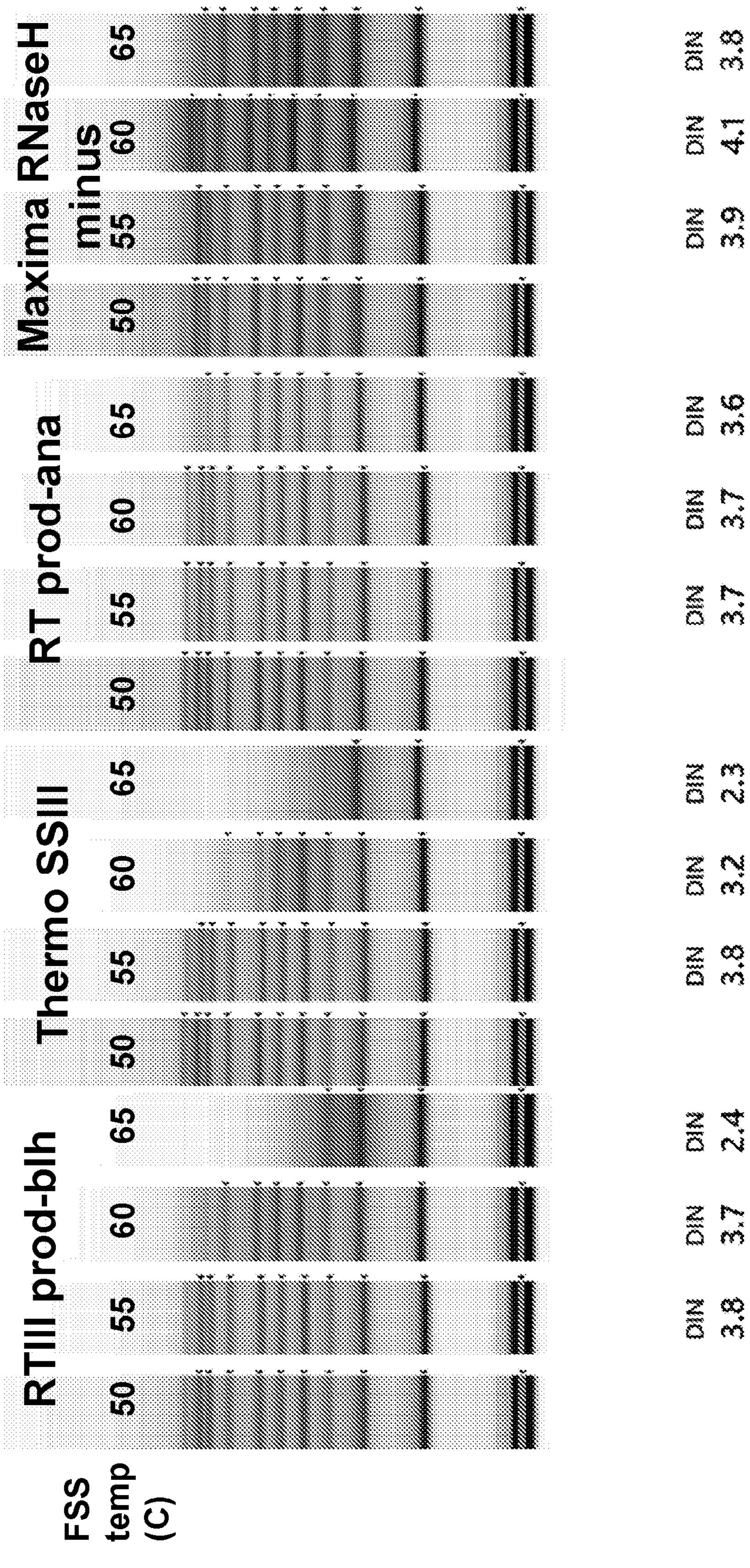
FIG. 2A shows enhanced thermo-activity of RT enzymes of the disclosure.

FIG. 2A shows RT prod-ana has enhanced thermo-activity. In an RNA ladder assay, 10 polyA RNA transcripts from 0.5 kb to 9 kb are used as RNA input into first strand synthesis (FSS). Specifically, FSS reactions were generated on ice by mixing 500 ng of Millennium RNA ladder (Millennium™ RNA Markers), 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, and 200 U specified reverse transcriptase. FSS was run at various temperatures (42-65° C.) and thermostability and processivity of the RT variants were analyzed on an electrophoresis tool (e.g., gDNA TAPESTATION instrument, Agilent). For example, prod-blh, prod-ana, Thermo SSIII, and Thermo Maxima RNaseH minus were run in the RNA ladder assay wherein FSS was employed at 50, 55, 60 or 65° C. for 30 minutes. Processivity of the reverse transcriptases was assessed qualitatively by the conversion, or lack thereof, of the higher MW RNA transcripts to cDNA.

The gDNA tapestation and resulting cDNA products from the RNA ladder assay is shown in FIG. 2A. Transcript length at various temperatures aligns with thermostability of the enzymes. Prod-blh converts the entire RNA ladder to cDNA when FSS temperature is performed at 42° C. or 50° C. When FSS temperatures are elevated to 60° C. or 65° C. the entire RNA ladder is not converted to cDNA. Prod-blh has very competitive cDNA conversion across all temperatures to Thermo SSIII reverse transcriptase. Prod-ana converts the entire RNA ladder to cDNA when FSS temperature is performed at 42° C., 50° C., or 60° C. When FSS temperatures are elevated to 65° C. the upper MW RNA transcript is not converted to cDNA. Prod-ana has very competitive cDNA conversion across all temperatures to Thermo Maxima RNaseH minus reverse transcriptase. RT prod-ana has enhanced thermostability and processivity compared to SSIII and competitive thermostability and processivity compared to Maxima RNaseH minus. RT variants of the disclosure were run in triplicates in a thermal shift assay to assess enzyme thermostability.

Figure 2B:
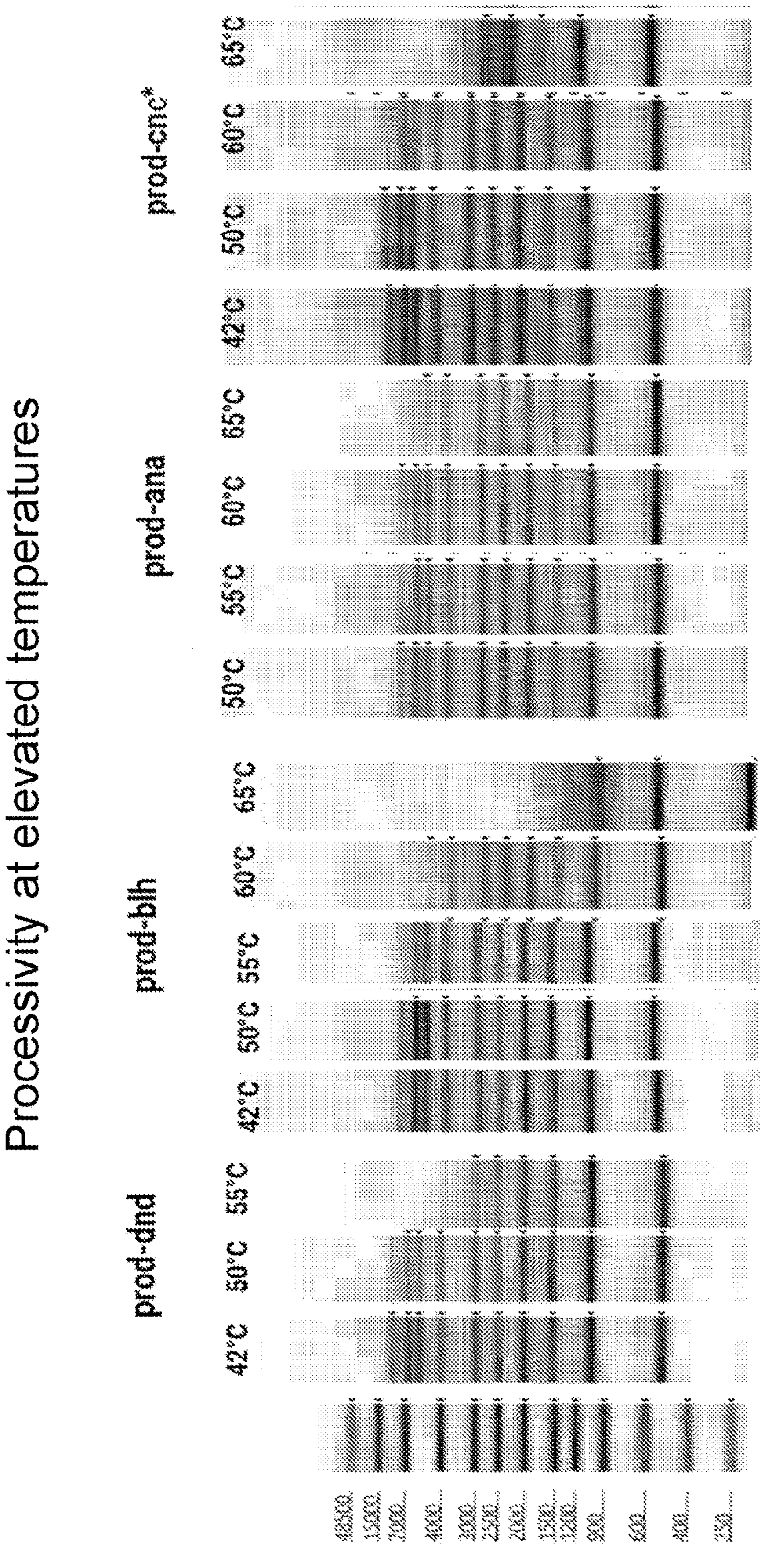
FIG. 2B shows processivity of RT enzymes of embodiments of the disclosure at elevated temperatures.

FIG. 2B shows processivity of RT enzymes of embodiments of the disclosure at elevated temperatures.

FSS reactions were generated on ice by mixing 500 ng of Millenium RNA ladder (Millennium™ RNA Markers), 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, and 200 U reverse transcriptase. FSS was run at various temperatures (42-65° C.) and thermostability and processivity of the RT variants were analyzed on a gDNA tapestation. Processivity of the reverse transcriptases was assessed qualitatively by the conversion, or lack thereof, of the higher MW RNA transcripts to cDNA.

The gDNA tapestation and resulting cDNA products from the RNA ladder assay is shown in FIG. 2B. Transcript length at various temperatures aligns with thermostability of the enzymes:

1. There is no cDNA conversion when no RT is present (data not shown)
2. All reverse transcriptases are able to convert all MW RNA transcripts to cDNA at 42° C. and 50° C.
3. At 55° C. Prod-dnd does not fully convert all transcripts of the RNA input to cDNA. Prod-blh, prod-ana, and prod-cnc are able to fully convert all transcripts at 55° C. and 60° C.
4. At 65° C. prod-ana converts 9 of the 10 polyA transcripts to cDNA.

Figure 3A:
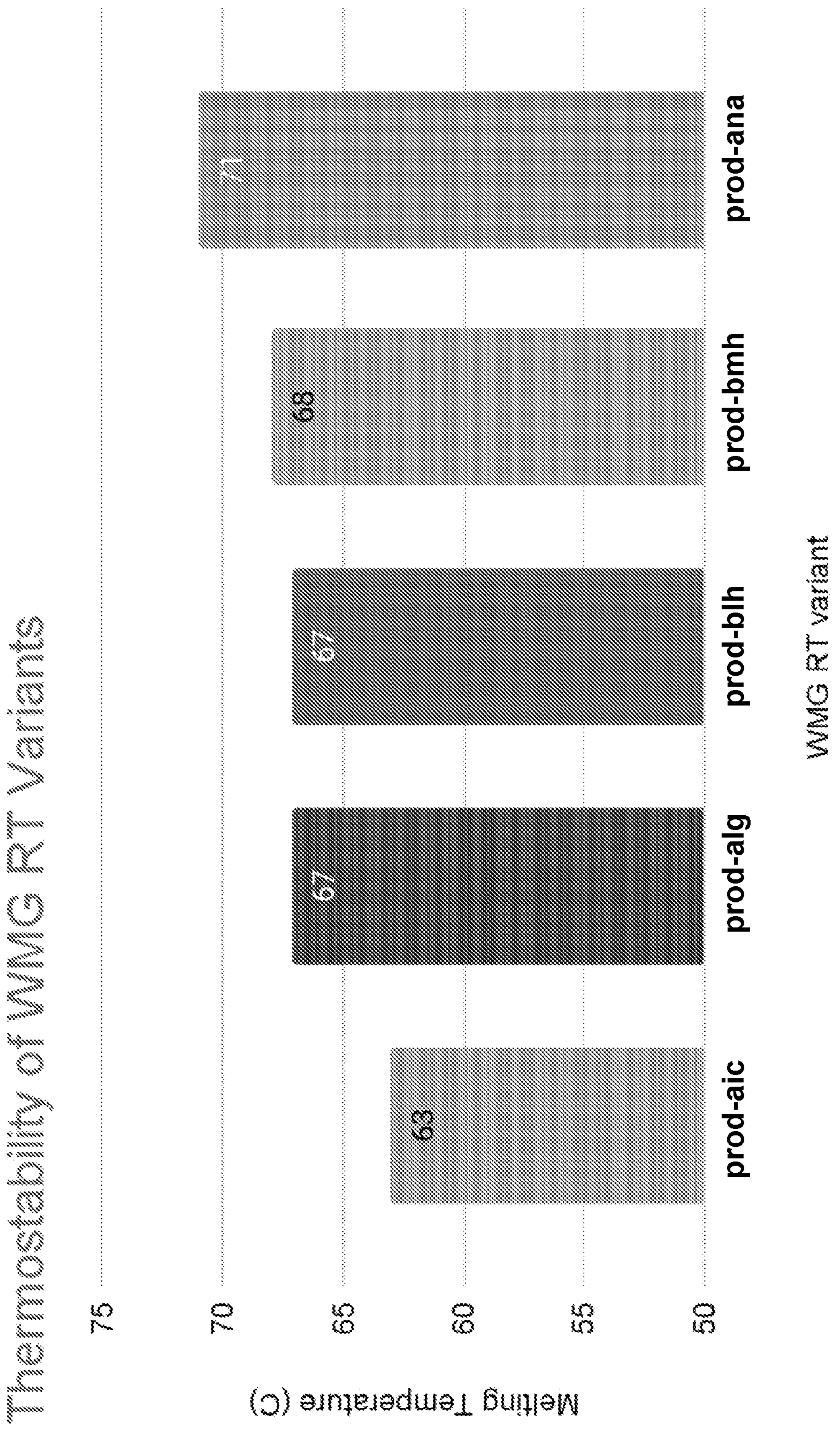
FIG. 3A shows thermostability of RT variant enzymes of the disclosure.

FIG. 3A shows thermostability of RT variants. WMG RT variants were run in triplicates in a thermal shift assay to assess enzyme thermostability. RT variants of the disclosure were run in triplicates in a thermal shift assay (GloMelt; Biotium) to assess enzyme thermostability. Biotium GloMelt manufacturing protocols were followed, and a thermal ramp gradient was employed. As the enzyme unfolds fluorescence signal increases and the inflexion point of the curves indicates the melting temperature for that enzyme.

Figure 3B:
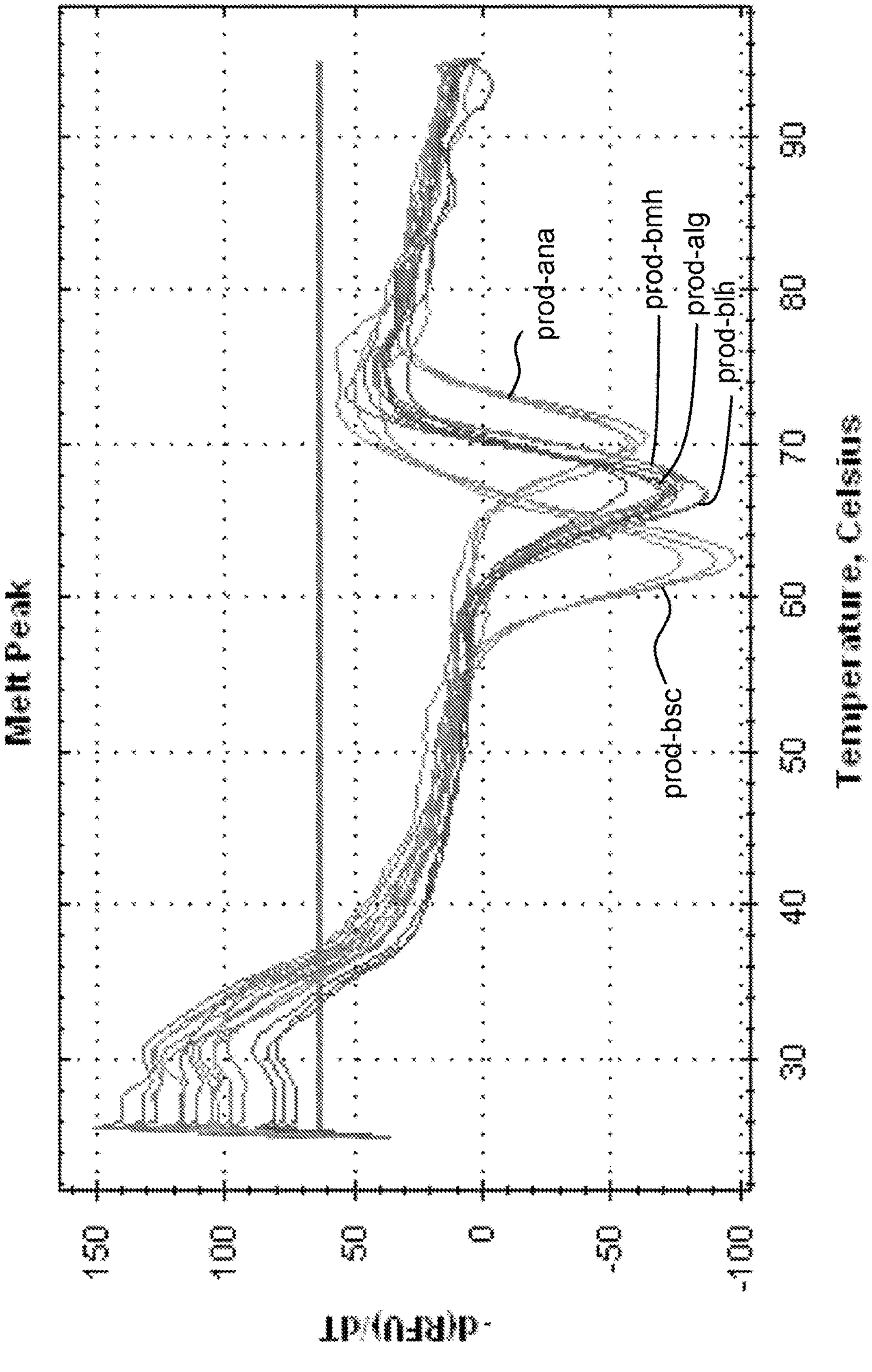
FIG. 3B shows melt curves indicative of thermostability.

FIG. 3B shows a melt curve that indicates that the RTs tested have various degrees of thermostability: RTII<prod-alg=RTIII<prod-bmh<prod-ana. Here, prod-ana exhibits a substantial increase in thermal stability compared to RTII and RTIII. As shown, prod-aic (RTII) exhibits a melt curve at 63° C., prod-alg exhibits a melt curve at 67° C., prod-blh (RTIII) exhibits a melt curve at 67° C., prod-bmh exhibits a melt curve at 68° C. and prod-ana exhibits a melt curve at 71° C. To melt curve indicates that the RTs tested have various degrees of thermostability.

Figure 3C:
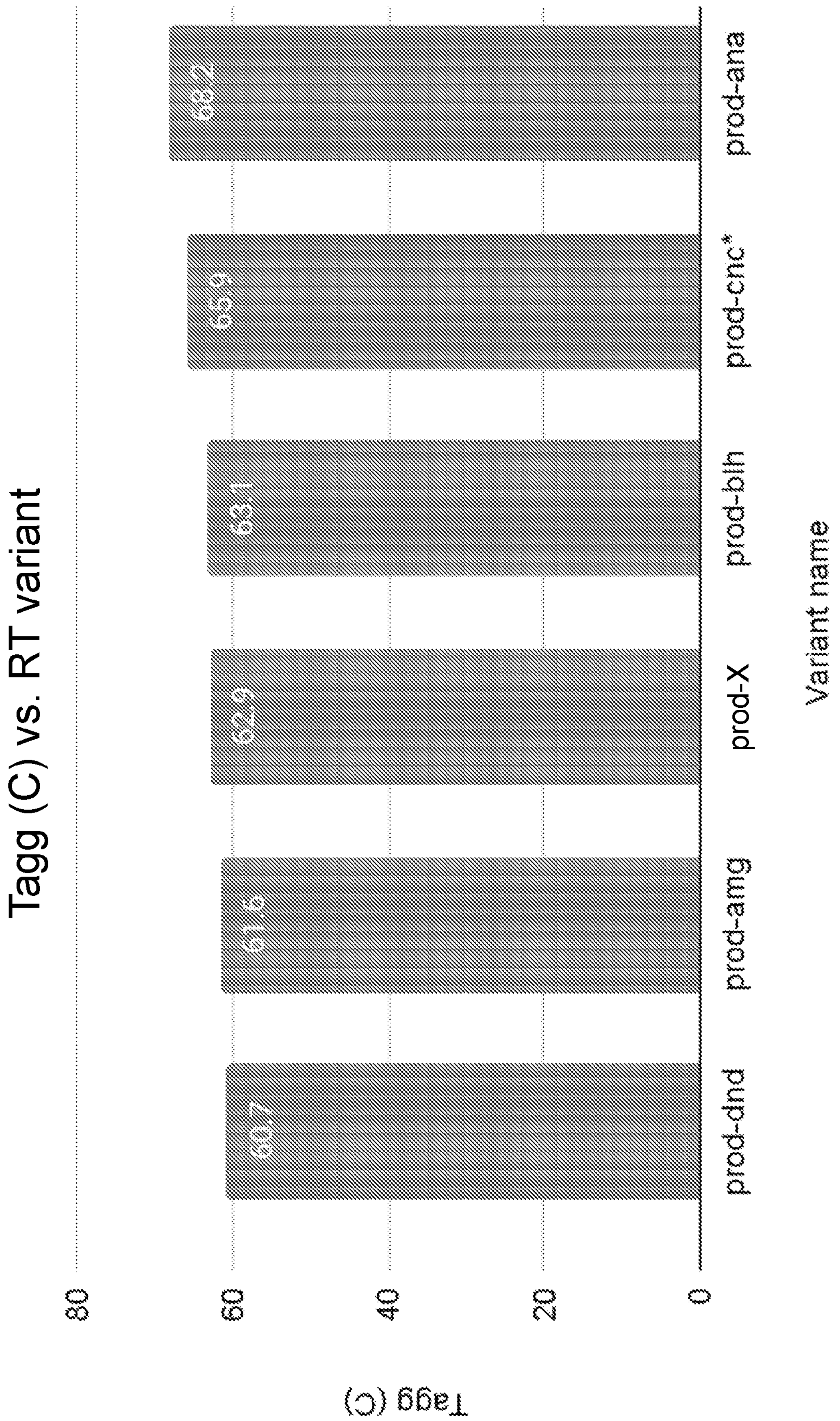
FIG. 3C shows thermal ramp assay results of embodiments of RT enzymes of the disclosure.
Figure 3E:
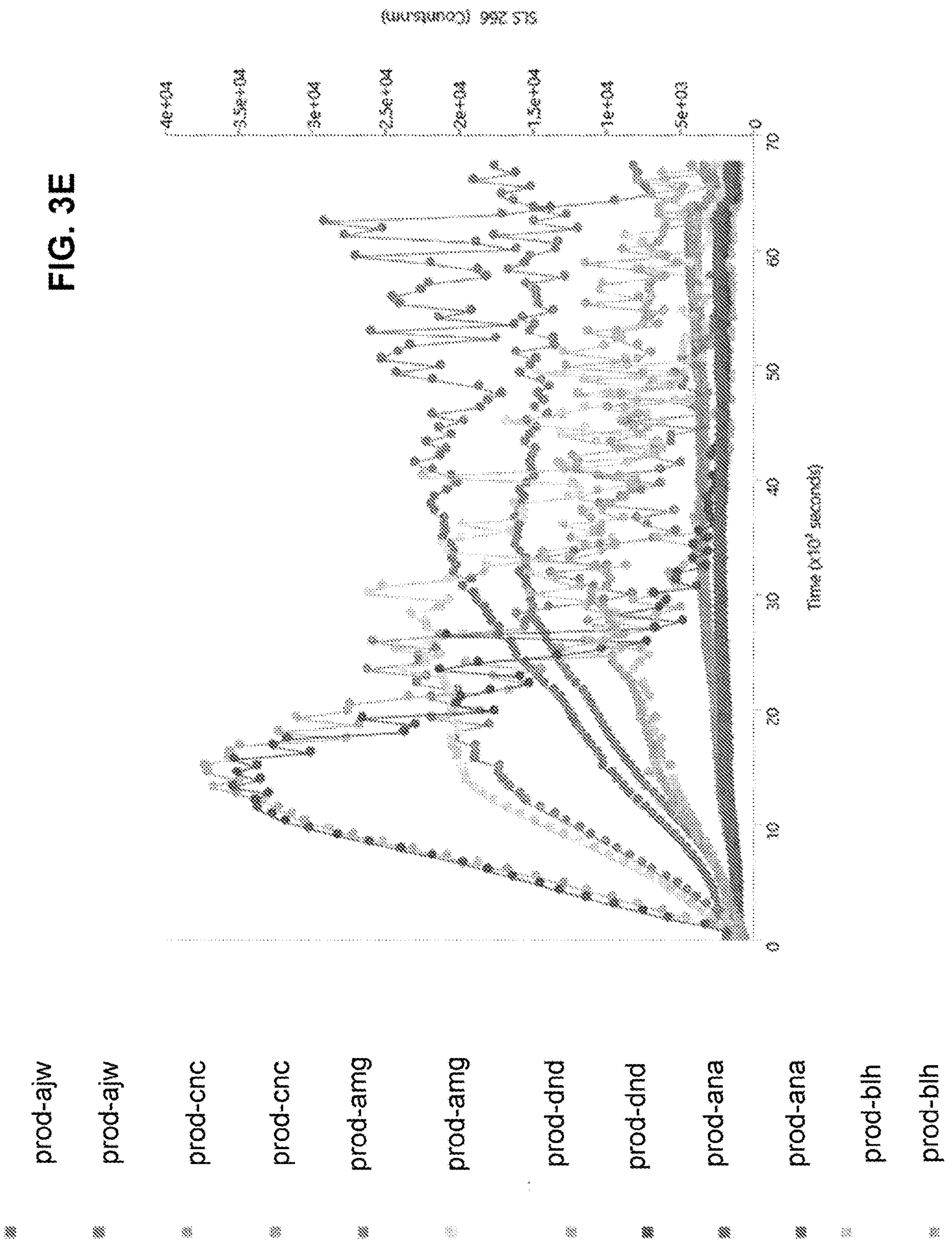
FIG. 3E shows isothermal reaction incubation for embodiments of RT enzymes of the disclosure

FIGS. 3C-3E show the results of further assessment of aggregation temperature and thermostability of reverse transcriptases of the discloser.

FIG. 3C shows thermal ramp assay results of embodiments of RT enzymes of the disclosure. RT variants were run in triplicates on the Unchained Labs Uncle instrument in a thermal ramp assay using static light scattering (SLS) to assess the onset of aggregation. A 266 nm laser was used to monitor the amount of light scattered while a 15° C. to 95° C. thermal ramp was applied to the samples. All RT variants were diluted to 0.25 mg/mL in the following buffer system. 60 mM Tris-HCl (pH=8.0), 75 mM KCl, 50 mM NaCl, 25% (v/v) Glycerol, 10 mM DTT, 3 mM $MgCl_2$. An increase in the amount of light scattered directly measures the level of aggregation occurring. Aggregation onset almost always occurs after a melting event occurring within the protein.

FIG. 3D shows a table of results for the thermal ramp assay of FIG. 3C for the RT variants tested. Results:

1. prod-dnd shows the lowest thermal stability with the lowest aggregation onset temperature of 60.7° C.
2. prod-ana shows the highest thermal stability with the highest aggregation onset temperature of 68.2° C.
3. prod-blh shows moderate thermal stability with an aggregation onset temperature between that of prod-dnd and prod-ana at 63.1° C.

FIG. 3E shows isothermal reaction incubation for embodiments of RT enzymes of the disclosure. RT variants were run in triplicates on the Unchained Labs Uncle instrument in an isothermal assay using static light scattering (SLS) to assess the onset of aggregation. A 266 nm laser was used to monitor the amount of light scattered while samples were held at 50° C. for roughly 20 hours. All RT variants were diluted to 0.25 mg/mL in the following buffer system: 60 mM Tris-HCl (pH=8.0), 75 mM KCl, 50 mM NaCl, 25% (v/v) Glycerol, 10 mM DTT, 3 mM $MgCl_2$. An increase in the amount of light scattered directly measures the level of aggregation occurring. Aggregation rates can be determined by the increase in SLS counts over time.

1. prod-dnd shows the lowest thermal stability with the steepest aggregation rate.
2. prod-ana shows the highest thermal stability with the most horizontal aggregation rate.
3. prod-blh shows moderate thermal stability with an aggregation rate between that of prod-dnd and prod-ana.

RT-qPCR Yields in the Presence of Various Inhibitors

First strand synthesis (FSS) reactions were generated on ice by mixing 10 ng of total liver RNA, 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, 200 U specified reverse transcriptase in the +/−various inhibitors (see below). FSS was run at temperatures optimal for the various reverse transcriptases, 42° C. for prod-dnd or 50° C. for prod-blh and incubated for 25 minutes followed by qPCR to assess cDNA yield. qPCR reactions were generated by mixing 1× SsoAdvanced Universal SYBR Green Supermix, 10% of the FSS reaction, and 0.6 uM of primers that anneal to the 5' end of the beta-actin gene.

Figure 4A:
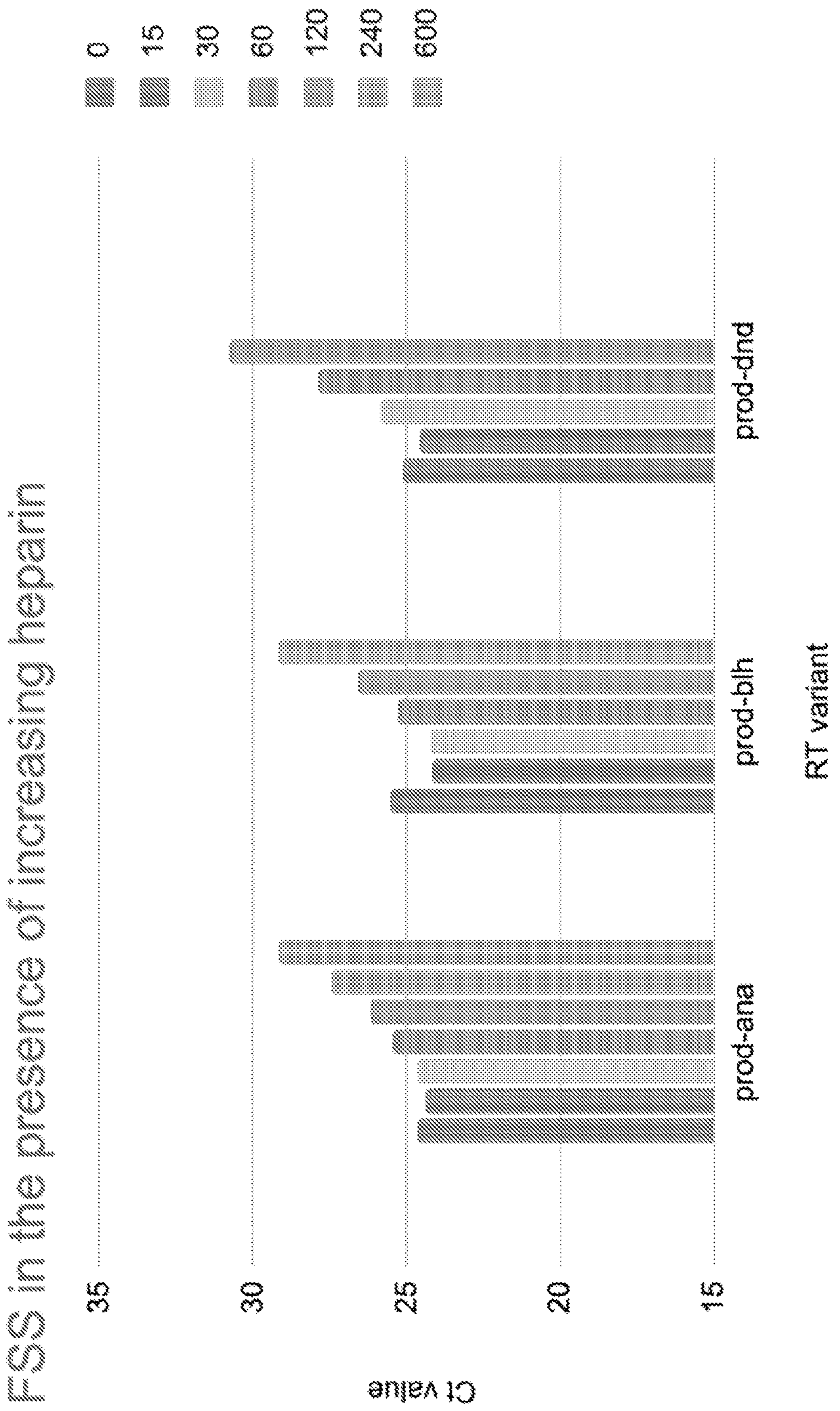
FIG. 4A shows tolerance to inhibition by heparin of embodiments of RT enzymes of the disclosure.
Figure 4B:
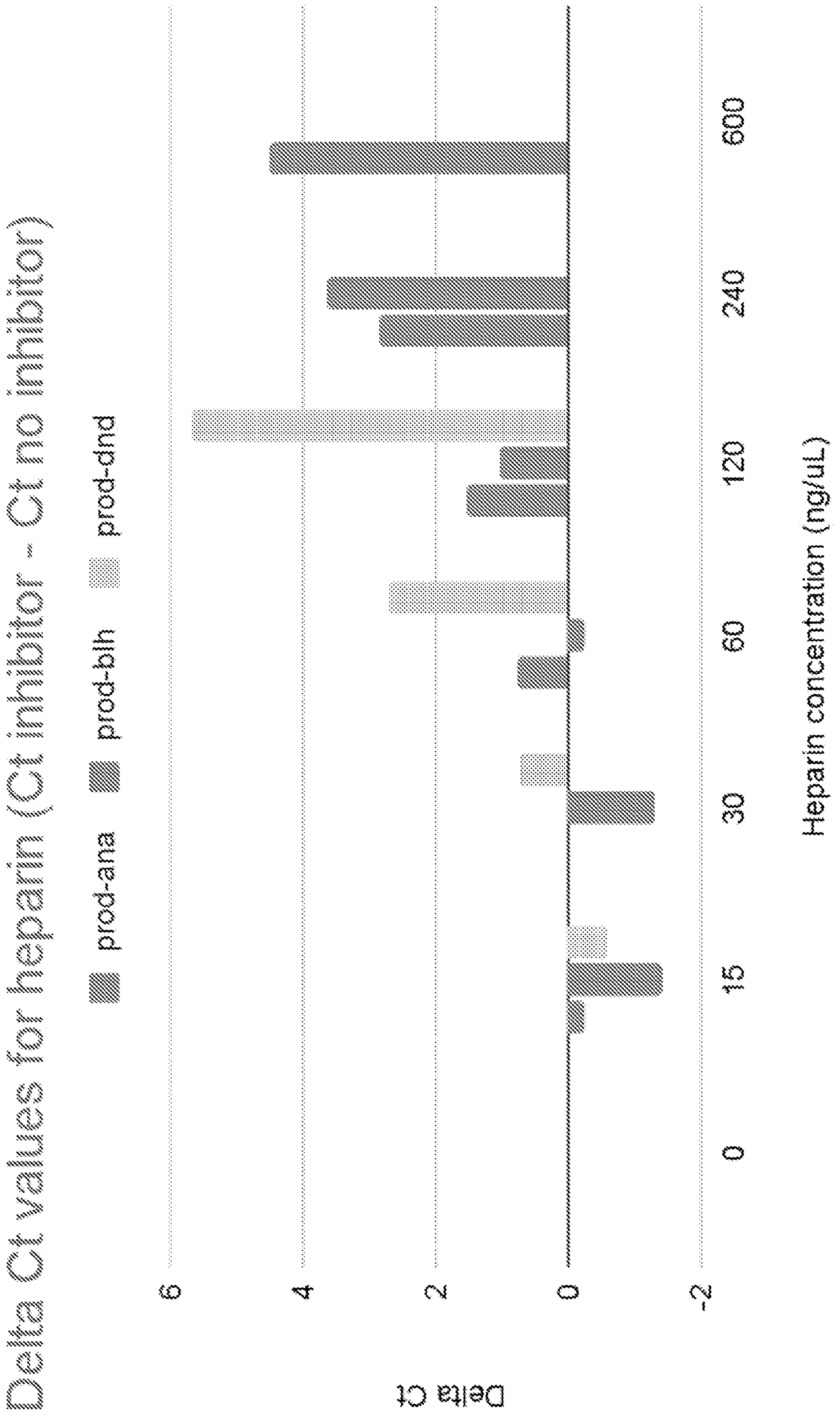
FIG. 4B shows changes in Ct values with increasing heparin concentration for RT enzymes of the disclosure.

FIGS. 4A and 4B show tolerance to inhibition by heparin of embodiments of RT enzymes of the disclosure. FSS was run as described above and in the presence of 0, 15, 30, 60, 120, 240, or 600 ng/uL of heparin. The resulting cDNA values were assessed via Ct values as shown in FIG. 4A.

FIG. 4B shows changes in Ct values with increasing heparin concentration for RT enzymes of the disclosure. Results are summarized below:

1. No inhibition was observed for all RT variants at 15 and 30 ng/uL of heparin.
2. Prod-dnd had the lowest yield (~10 fold or >lower yield) in the presence of >=60 ng/uL and no cDNA was generated at concentrations>120 ng/uL of heparin.
3. Prod-blh had ~4-10 fold lower cDNA yield in the presence of 240 ng/uL compared to prod-ana and no cDNA was generated when 600 ng/uL of heparin was added.
4. Prod-ana had the highest cDNA yield across a broad range of heparin concentrations and cDNA was generated at every heparin concentration tested.

Figure 4C:
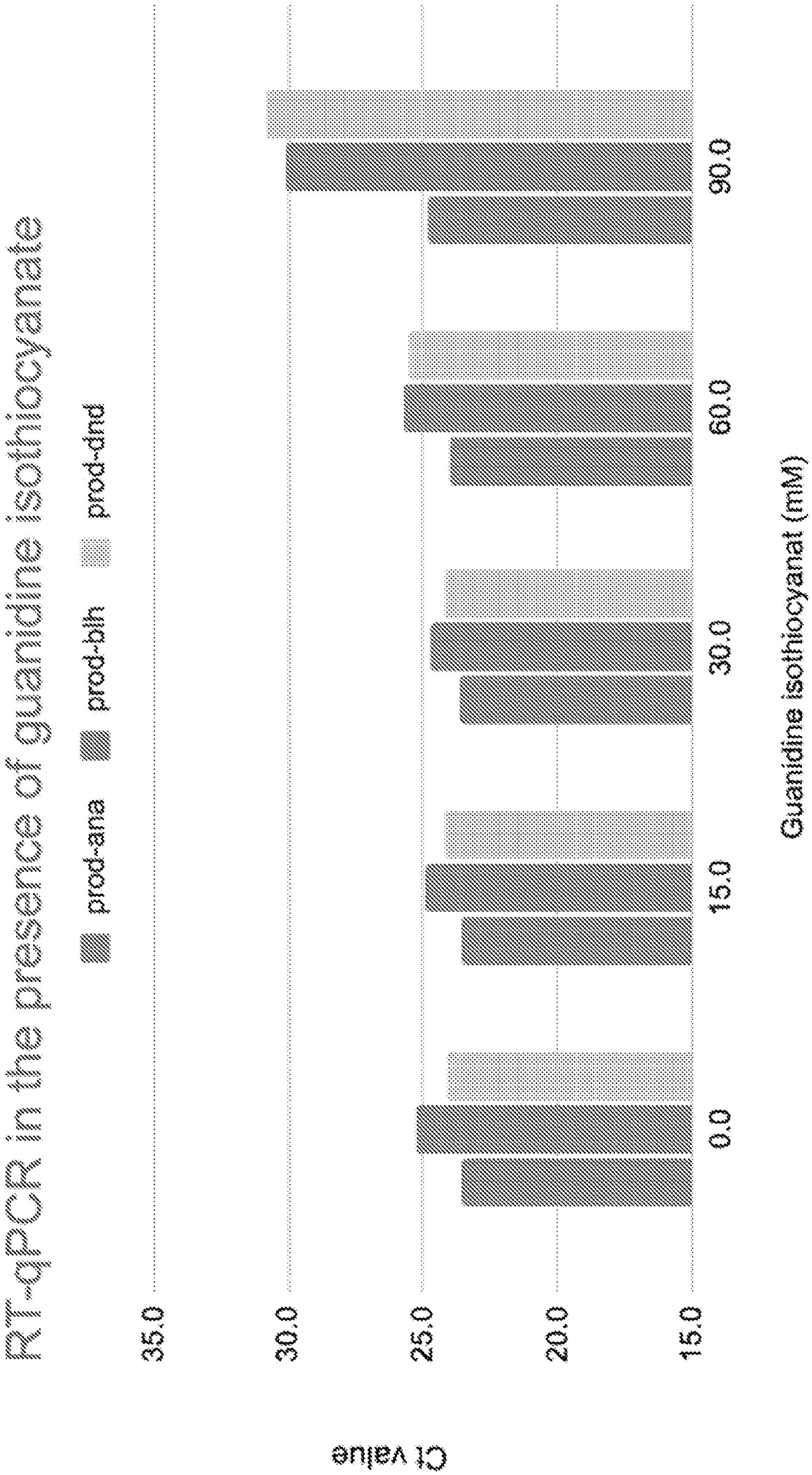
FIG. 4C shows tolerance to inhibition by guanidine isothiocyanate of embodiments of RT enzymes of the disclosure.
Figure 4D:
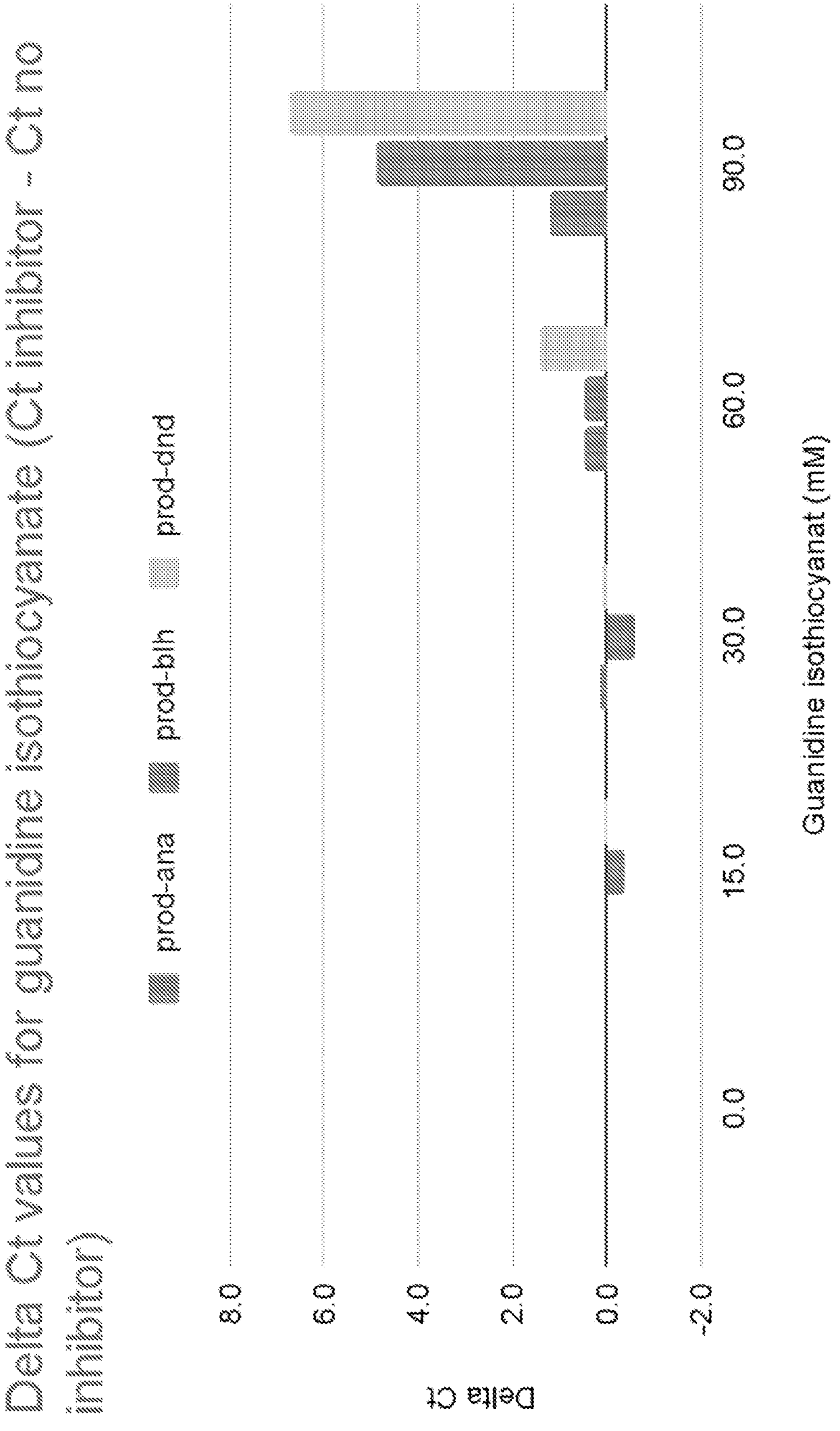
FIG. 4D shows change in Ct values with increasing guanidine isothiocyanate concentration for RT enzymes of the disclosure.

FIGS. 4C and 4D show tolerance to inhibition by guanidine isothiocyanate of embodiments of RT enzymes of the disclosure.

FSS was run as described above in the presence of 0, 15, 30, 60 or 90 mM of guanidine isothiocyanate. The resulting cDNA values were assessed via Ct values as shown in FIG. 4C.

FIG. 4D shows change in Ct values for RT variants of the disclosure with increasing guanidine isothiocyanate concentration. Results are summarized below:

1. No inhibition, or very minimal inhibition, was observed for all RT variants at 30 and 60 mM guanidine isothiocyanate.
2. Prod-dnd showed the greatest inhibition and was inhibited ~4 fold at 60 mM inhibitor and ~100 fold at 90 mM inhibitor.
3. Prod-blh were inhibited by ~4 fold at 60 mM inhibitor and >10 fold at 90 mM inhibitor.
4. Prod-ana had the highest cDNA yield across a broad range of guanidine isothiocyanate concentrations and was inhibited by ~3 fold at 90 mM inhibitor.

Figure 4E:
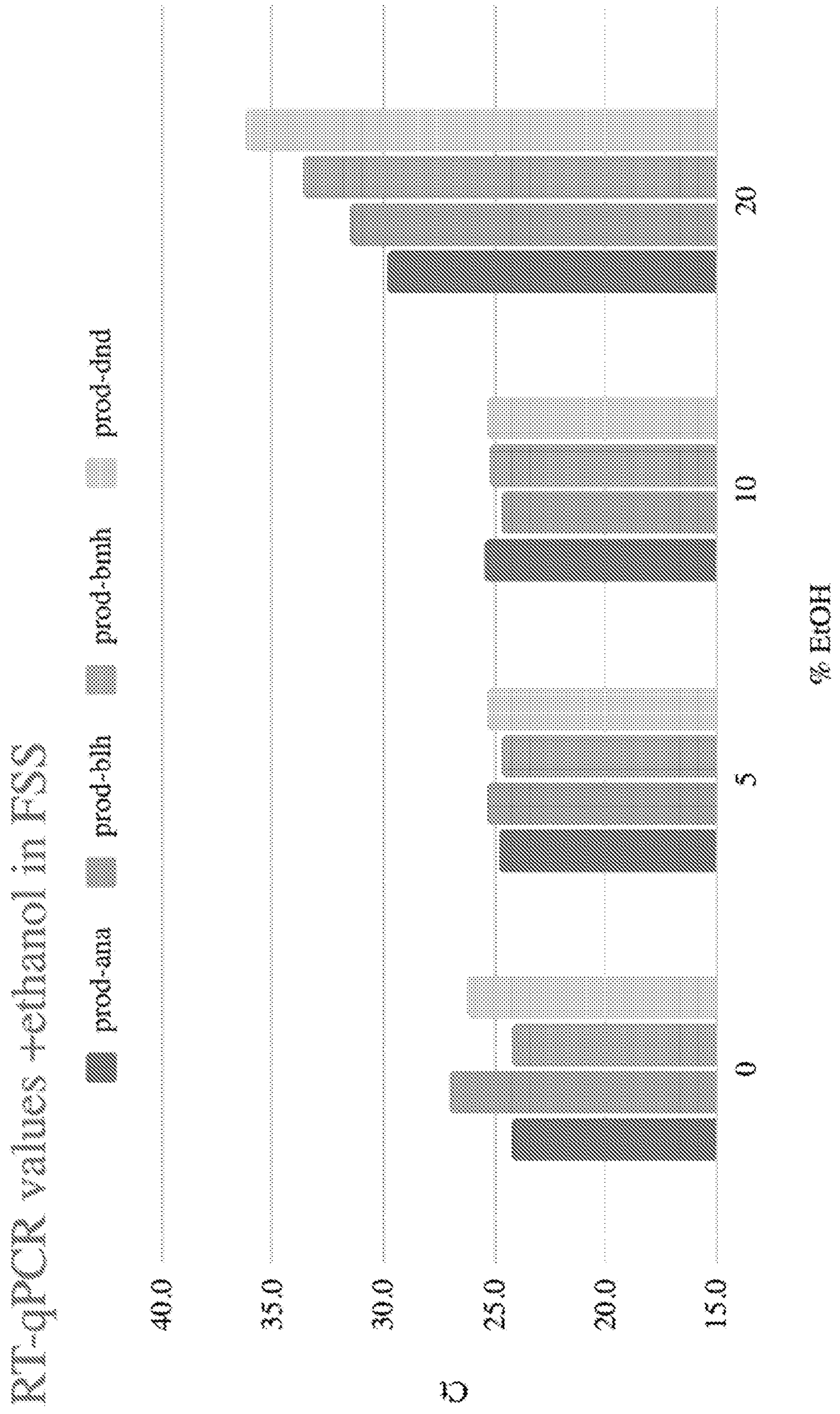
FIG. 4E shows tolerance to inhibition by ethanol of embodiments of RT enzymes of the disclosure

FIG. 4E shows tolerance to inhibition by ethanol of embodiments of RT enzymes of the disclosure.

FSS was run as described above in the presence of 0, 5, 10 or 20% ethanol. The resulting cDNA values were assessed via Ct values as shown in FIG. 4E. FIG.

Figure 4F:
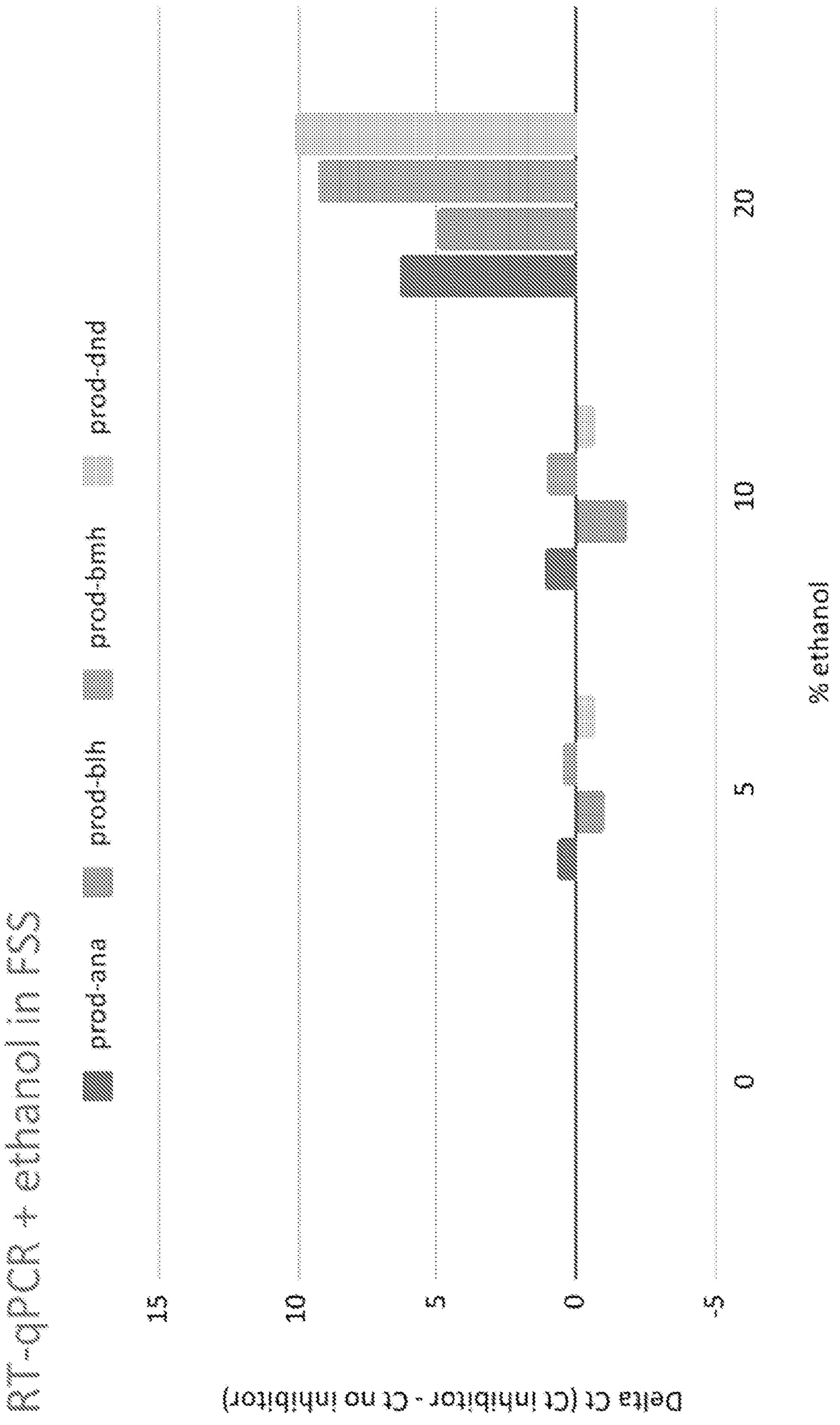
FIG. 4F shows change in Ct values with increasing ethanol concentration for RT enzymes of the disclosure.
Figure 5:
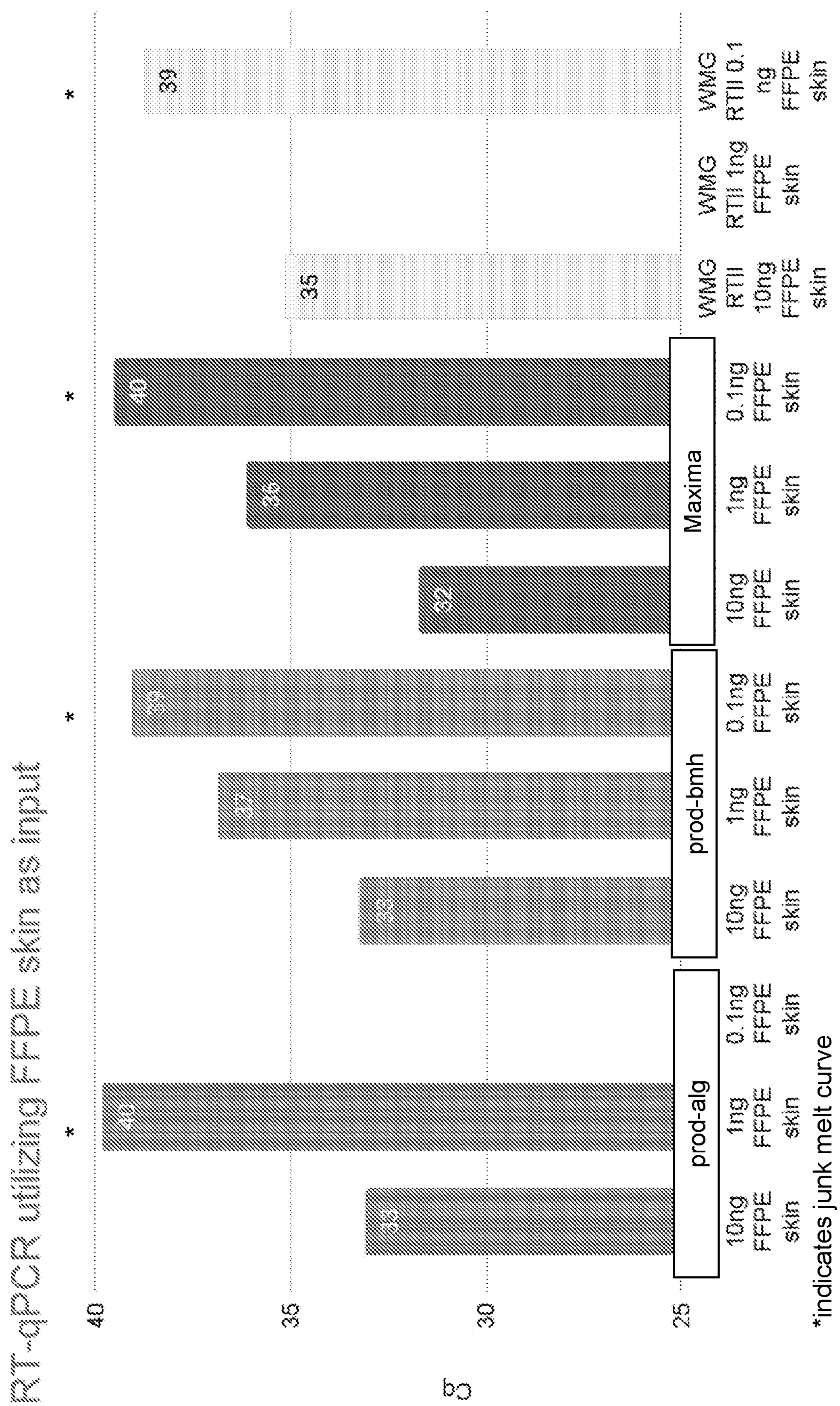
FIG. 5 shows cDNA yields of RT enzymes of the disclosure.

FIG. 4F shows change in Ct values with increasing ethanol concentration for RT enzymes of the disclosure. Results are summarized below:

1. No inhibition, or very minimal inhibition, was observed for all RT variants at 5 and 10% ethanol.
2. Prod-bmh and prod-dnd were inhibited by >~100 fold at 20% ethanol.
3. Prod-ana and Prod-blh were inhibited by <100 fold at 20% ethanol FIG. 5 shows prod-bmh RT has competitive cDNA yields from FFPE samples as Maxima. First strand synthesis (FSS) reactions were generated on ice by mixing 10, 1, or 0.1 ng of FFPE RNA isolated from skin tissue, 1× reaction buffer (50 mM Tris-HCl pH 8.3, 75 mM KCl, 3 mM $MgCl_2$), 10 U Murine RNase Inhibitor, 5 uM oligo-dT(20), 0.5 mM dNTPs, and 200 U specified reverse transcriptase. FSS was run at 42° C. for 25 minutes followed by qPCR to assess cDNA yield. qPCR reactions were generated by mixing 1× SsoAdvanced Universal SYBR Green Supermix, 10% of the FSS reaction, and 0.6 uM of a primers that anneal to the 5' end of a Beta-actin gene.

Results: The resulting cDNA values were assessed via Ct values and are shown in FIG. 5. Note, asterisk represent a nonspecific melt curve was generated and no specific product was made.

1. Prod-dnd had the lowest yield (~4 fold less than prod-alg and prod-bmh) and only generated specific cDNA product at the 10 ng FFPE RNA input.
2. Prod-alg had equivalent cDNA yields to prod-bmh at 10 ng of FFPE RNA input but was unable to generate specific cDNA product at lower RNA inputs.
3. Prod-bmh generated specific product at 10 ng and 1 ng of FFPE RNA input. cDNA yield was competitive with Maxima RNaseH minus' Reverse Transcriptase.
4. WMG prod-ana has competitive yields and efficiency scores in RT-qPCR as Maxima at 50° C. and 60° C.

Additional further mutations that may optionally be included include one or any combination of S27T, V43K, A46P, L48I, A54P, S56A, S60W, Q68K, L72Q, L72R, E123Q, Y133C, G138S, T163K, M177R, D200H, I212T, I218T, T231E, S232T, L234E, Q237E, A242D, N249E, Q265E, K264Q, K267T, L272I T281S, G290K, N335Q P338E, D339E, Y344F, Q345D E346D, Q349R, Y376F, V413I, T420V, G424D, A442S, V433T, V444I, D518E, G524D, L528F, A554P, Q562E, D583N, K550S, D615E, A619E, F625W/H, R629K, H642D, and K658E.

Sequences

The following sequences may be referred to or used within embodiments of the disclosure. In wtMMLV-RT-aa (SEQ ID NO: 1), position 1 is homologous to position 34 in each of: prod-dnd-aa (SEQ-ID NO 2); prod-ana-aa (SEQ ID NO: 4); prod-amg-aa (SEQ ID NO: 5); prod-asb-aa (SEQ ID NO: 6); prod-bmh-aa (SEQ ID NO: 7); prod-cnc-aa (SEQ ID NO: 8); prod-cmi-aa (SEQ ID NO: 9); prod-bnb-aa (SEQ ID NO: 10); prod-bsc-aa (SEQ ID NO: 11); prod-csd-aa (SEQ ID NO: 12); and prod-dsf-aa (SEQ ID NO: 13). That is, a position X in SEQ ID NO: 1 is homologous to position X+33 in any of SEQ ID Nos: 2 and 4-14.

>wtMMLV-RT-aa (SEQ ID NO: 1)

TLNIEDEHRL HETSKEPDVS LGSTWLSDFP QAWAETGGMG LAVRQAPLII

PLKATSTPVS IKQYPMSQEA RLGIKPHIQR LLDQGILVPC QSPWNTPLLP

VKKPGTNDYR PVQDLREVNK RVEDIHPTVP NPYNLLSGLP PSHQWYTVLD

LKDAFFCLRL HPTSQPLFAF EWRDPEMGIS GQLTWTRLPQ GFKNSPTLFD

EALHRDLADF RIQHPDLILL QYVDDLLLAA TSELDCQQGT RALLQTLGNL

GYRASAKKAQ ICQKQVKYLG YLLKEGQRWL TEARKETVMG QPTPKTPRQL

REFLGTAGFC RLWIPGFAEM AAPLYPLTKT GTLFNWGPDQ QKAYQEIKQA

LLTAPALGLP DLTKPFELFV DEKQGYAKGV LTQKLGPWRR PVAYLSKKLD

-continued

PVAAGWPPCL RMVAAIAVLT KDAGKLTMGQ PLVILAPHAV EALVKQPPDR

WLSNARMTHY QALLLDTDRV QFGPVVALNP ATLLPLPEEG LQHNCLDILA

EAHGTRPDLT DQPLPDADHT WYTDGSSLLQ EGQRKAGAAV TTETEVIWAK

ALPAGTSAQR AELIALTQAL KMAEGKKLNV YTDSRYAFAT AHIHGEIYRR

RGLLTSEGKE IKNKDEILAL LKALFLPKRL SIIHCPGHQK GHSAEARGNR

MADQAARKAA ITETPDTSTL L

>prod-dnd-aa (SEQ-ID NO 2)

MGGSHHHHHH GMASMTGGQQ MGRDLYDDDD KHMTLNIEDE HRLHETSKEP

DVSLGSTWLS DFPQAWAETG GMGLAVRQAP LIIPLKATST PVSIKQYPMS

QEARLGIKPH IQRLLDQGIL VPCQSPWNTP LLPVKKPGTN DYRPVQDLRE

VNKRVEDIHP TVPNPYNLLS GLPPSHQWYT VLDLKDAFFC LRLHPTSQPL

FAFEWRDPEM GISGQLTWTR LPQGFKNSPT LFDEALHRDL ADFRIQHPDL

ILLQYVDDLL LAATSELDCQ QGTRALLQTL GNLGYRASAK KAQICQKQVK

YLGYLLKEGQ RWLTEARKET VMGQPTPKTP RQLREFLGTA GFCRLWIPGF

AEMAAPLYPL TKTGTLFNWG PDQQKAYQEI KQALLTAPAL GLPDLTKPFE

LFVDEKQGYA KGVLTQKLGP WRRPVAYLSK KLDPVAAGWP PCLRMVAAIA

VLTKDAGKLT MGQPLVILAP HAVEALVKQP PDRWLSNARM THYQALLLDT

DRVQFGPVVA LNPATLLPLP EEGLQHNCLD ILAEAHGTRP DLTDQPLPDA

DHTWYTGGSS LLQEGQRKAG AAVTTETEVI WAKALPAGTS AQRAQLIALT

QALKMAEGKK LNVYTNSRYA FATAHIHGEI YRRRGLLTSE GKEIKNKDEI

LALLKALFLP KRLSIIHCPG HQKGHSAEAR GNRMADQAAR KAAITETPDT

STLL

>prod-dnd-nt (SEQ-ID NO 3)

ATGGGGGGTT CTCATCATCA TCATCATCAT GGTATGGCTA GCATGACTGG

TGGACAGCAA ATGGGTCGGG ATCTGTACGA CGATGACGAT AAGCATATGA

CCCTAAATAT AGAAGATGAG CACCGGCTAC ATGAGACCTC AAAAGAGCCA

GATGTTTCTC TAGGGTCCAC ATGGTTATCG GATTTCCCGC AAGCTTGGGC

TGAAACGGGG GGTATGGGGC TTGCTGTACG CCAGGCGCCC CTTATTATTC

CTCTTAAGGC AACAAGCACC CCCGTCAGCA TCAAACAATA CCCCATGTCA

CAAGAAGCGC GTTTGGGTAT TAAACCGCAC ATTCAACGCT TGCTGGACCA

AGGGATCCTT GTCCCCTGTC AGTCTCCATG GAACACGCCG CTGTTACCGG

TCAAGAAGCC TGGTACAAAC GACTACCGTC CTGTACAGGA TTTGCGCGAG

GTAAATAAGC GTGTAGAGGA TATCCACCCC ACCGTGCCCA ACCCATACAA

CTTGTTGTCT GGTTTACCGC CTTCACATCA GTGGTATACG GTCCTTGATT

TGAAAGATGC ATTTTTCTGC CTGCGCTTGC ACCCTACGTC TCAGCCACTG

TTCGCATTCG AGTGGCGCGA CCCTGAAATG GGTATCAGTG GTCAGTTAAC

CTGGACACGC TTACCGCAAG GTTTCAAGAA TAGCCCGACC TTATTCGATG

AAGCACTTCA CCGCGATCTT GCCGATTTCC GCATCCAGCA CCCGGATCTT

ATTTTGTTGC AGTACGTAGA CGACCTGTTG TTGGCAGCCA CGTCGGAATT

GGATTGTCAG CAAGGAACAC GCGCGTTACT GCAAACTCTG GGTAATTTGG

GCTACCGTGC CTCCGCAAAG AAAGCGCAGA TCTGCCAAAA GCAAGTAAAA

-continued

TACTTAGGAT ATTTATTGAA GGAGGGCCAG CGTTGGCTTA CAGAAGCTCG

CAAAGAAACT GTGATGGGAC AACCTACGCC TAAAACTCCT CGTCAGCTTC

GCGAATTCCT GGGAACAGCG GGGTTCTGTC GCCTGTGGAT TCCTGGTTTT

GCAGAGATGG CGGCGCCCCT TTACCCACTG ACCAAAACAG GGACATTATT

TAACTGGGGT CCCGATCAGC AGAAGGCCTA TCAGGAGATC AAGCAGGCTT

TACTTACAGC GCCAGCCTTA GGGTTACCGG ACCTTACGAA GCCCTTTGAG

TTATTCGTCG ACGAGAAACA GGGCTATGCA AAGGGTGTAC TGACCCAGAA

GTTGGGGCCG TGGCGTCGCC CGGTCGCCTA TTTGTCGAAA AAACTGGATC

CCGTGGCGGC CGGGTGGCCA CCTTGCCTGC GTATGGTTGC AGCTATTGCT

GTATTAACAA AAGACGCAGG AAAATTAACG ATGGGACAAC CGTTAGTCAT

TCTTGCGCCG CACGCAGTAG AAGCACTGGT AAAGCAACCG CCCGATCGCT

GGTTATCGAA CGCGCGCATG ACGCACTATC AGGCGTTGTT ACTTGATACA

GATCGTGTAC AGTTTGGCCC TGTCGTTGCA TTGAACCCAG CCACGCTGTT

ACCTCTTCCG GAAGAAGGAT TACAACACAA CTGTCTGGAC ATCCTGGCGG

AAGCTCATGG AACCCGCCCT GACTTGACAG ACCAACCGTT ACCCGACGCT

GATCATACCT GGTATACCGG GGGTTCGTCG CTTTTGCAGG AAGGGCAACG

TAAGGCAGGT GCAGCCGTAA CGACCGAGAC CGAAGTCATC TGGGCCAAGG

CCTTGCCAGC GGGGACTAGT GCCCAGCGTG CCCAATTAAT TGCCCTTACG

CAGGCATTAA AGATGGCTGA AGGAAAAAAG CTGAATGTAT ACACTAACAG

CCGCTACGCG TTCGCGACAG CGCATATTCA TGGAGAGATC TACCGTCGCC

GCGGACTTCT TACCTCCGAG GGTAAGGAGA TTAAGAACAA AGATGAGATT

CTGGCTTTGT TGAAGGCGTT GTTTTTGCCC AAACGTTTGT CAATCATTCA

CTGTCCCGGG CATCAAAAAG GGCACAGCGC CGAGGCCCGT GGTAACCGTA

TGGCAGACCA GGCCGCACGT AAAGCAGCCA TTACGGAGAC ACCTGATACG

AGTACGTTAC TTTAA

>prod-ana-aa (SEQ ID NO: 4)

MGGSHHHHHHGMASMTGGQQMGRDLYDDDDKHMTLNIEDEHRLHETSKEPDVSLGS

TWLSDFPQAWAETGGMGLAVRQAPLIIPLKATATPVSIKQYPMSQEARQGIKPHIQRLLD

QGILVPCQSPWNTPLLPVKKPGTNDYRPVQDLREVNKRVEDIHPTVPNPYNLLSSLPPSH

QWYTVLDLKDAFFCLRLHPKSQPLFAFEWRDPEMGISGQLTWTRLPQGFKNSPTLFDEA

LRRDLADFRIQHPDLILLQYVDDLLLAATTEEDCQQGTRALLQTLGELGYRASAKKAQI

CQKQVKYLGYLLKEGQRWLTEARKETVMKQPTPKTPRQLREFLGKAGFCRLWIPGFAE

MAAPLYPLTKTGTLFNWGPDQQKAFQEIKQALLTAPALGLPDLTKPFELFVDEKQGYA

KGVLTQKLGPWRRPVAYLSKKLDPVAAGWPPCLRMVAAIAVLVKDADKLTMGQPLVI

LAPHAVEALIKQPPDRWLSNARMTHYQALLLDTDRVQFGPVVALNPATLLPLPEEGLQ

HNCLDILAEAHGTRPDLTDQPLPDADHTWYTGGSSLLQEGQRKAGAAVTTETEVIWAK

ALPAGTSAQRAQLIALTQALKMAEGKKLNVYTNSRYAFATAHIHGEIYRRRGLLTSEGK

EIKNKEEILALLKALFLPKRLSIIHCPGHQKGDSAEARGNRMADQAARKAAITETPDTST

LLIENSSPNSRLIN

-continued

>prod-amg-aa (SEQ ID NO: 5)

MGGSHHHHHH GMASMTGGQQ MGRDLYDDDD KHMTLNIEDE HRLHETSKEP

DVSLGSMTWL SDFPQAWAET GGMGLAVRQA PLIIPLKATA TPVSIKQYPM

SQEARLGIKP HIQRLLDQGI LVPCQSPWNT PLLPVKKPGT NDYRPVQDLR

EVNKRVEDIH PTVPNPYNLL SSLPPSHQWY TVLDLKDAFF CLRLHPTSQP

LFAFEWRDPE MGISGQLTWT RLPQGFKNSP TLFDEALHRD LADFRIQHPD

LILLQYVDDL LLAATTEEDC QQGTRALLQT LGNLGYRASA KKAQICQKQV

KYLGYLLKEG QRWLTEARKE TVMKQPTPKT PRQLREFLGT AGFCRLWIPG

FAEMAAPLYP LTKTGTLFNW GPDQQKAFQE IKQALLTAPA LGLPDLTKPF

ELFVDEKQGY AKGVLTQKLG PWRRPVAYLS KKLDPVAAGW PPCLRMVAAI

AVLVKDADKL TMGQPLVILA PHAVEALIKQ PPDRWLSNAR MTHYQALLLD

TDRVQFGPVV ALNPATLLPL PEEGLQHNCL DILAEAHGTR PDLTDQPLPD

ADHTWYTGGS SLLQEGQRKA GAAVTTETEV IWAKALPAGT SAQRAQLIAL

TQALKMAEGK KLNVYTNSRY AFATAHIHGE IYRRRGLLTS EGKEIKNKEE

ILALLKALFL PKRLSIIHCP GHQKGHSAEA RGNRMADQAA RKAAITETPD

TSTLLIENSS PNSRLIN

>prod-asb-aa (SEQ ID NO: 6)

MGGSHHHHHH GMASMTGGQQ MGRDLYDDDD KHMTLNIEDE HRLHETSKEP

DVSLGSTWLT DFPQAWAETG GMGLAKRQPP IIIPLKPTAT PVWIKQYPMS

KEARQGIKPH IQRLLDQGIL VPCQSPWNTP LLPVKKPGTN DYRPVQDLRE

VNKRVQDIHP TVPNPCNLLS SLPPSHQWYT VLDLKDAFFC LRLHPKSQPL

FAFEWRDPER GISGQLTWTR LPQGFKNSPT LFHEALHRDL ADFRTQHPDL

TLLQYVDDLL LAAETEEDCE QGTRDLLQTL GELGYRASAK KAQICQQEVT

YLGYILKEGQ RWLSEARKET VMKQPTPKTP RQLREFLGTA GFCRLWIPGF

AEMAAPLYPL TKTGTLFQWG EEQQKAFDDI KRALLTAPAL GLPDLTKPFE

LFVDEKQGFA KGVLTQKLGP WRRPVAYLSK KLDPVAAGWP PCLRMIAAIA

VLVKDADKLT MGQPLTILAP HAVESLIKQP PDRWLSNARM THYQALLLDT

DRVQFGPVVA LNPATLLPLP EEGLQHNCLD ILAEAHGTRP DLTDQPLPDA

EHTWYTGGSS FLQEGQRKAG AAVTTETEVI WASALPPGTS AQRAQLIALT

QALKMAEGKK LNVYTNSRYA FATAHIHGEI YRRRGLLTSE GKEIKNKEEI

LELLKALWLP KKLAIIHCPG HQKGDSAEAR GNRMADQAAR EAAITETPDT

STLLIENSSP NSRLIN

>prod-bmh-aa (SEQ ID NO: 7)

MGGSHHHHHH GMASMTGGQQ MGRDLYDDDD KHMTLNIEDE HRLHETSKEP

DVSLGSMTWL SDFPQAWAET GGMGLAVRQA PLIIPLKATA TPVSIKQYPM

SQEARLGIKP HIQRLLDQGI LVPCQSPWNT PLLPVKKPGT NDYRPVQDLR

EVNKRVEDIH PTVPNPYNLL SSLPPSHQWY TVLDLKDAFF CLRLHPTSQP

LFAFEWRDPE MGISGQLTWT RLPQGFKNSP TLFDEALRRD LADFRIQHPD

LILLQYVDDL LLAATTEEDC QQGTRALLQT LGNLGYRASA KKAQICQKQV

KYLGYLLKEG QRWLTEARKE TVMKQPTPKT PRQLREFLGK AGFCRLWIPG

-continued

FAEMAAPLYP LTKTGTLFNW GPDQQKAFQE IKQALLTAPA LGLPDLTKPF

ELFVDEKQGY AKGVLTQKLG PWRRPVAYLS KKLDPVAAGW PPCLRMVAAI

AVLVKDADKL TMGQPLVILA PHAVEALIKQ PPDRWLSNAR MTHYQALLLD

TDRVQFGPVV ALNPATLLPL PEEGLQHNCL DILAEAHGTR PDLTDQPLPD

ADHTWYTGGS SLLQEGQRKA GAAVTTETEV IWAKALPAGT SAQRAQLIAL

TQALKMAEGK KLNVYTNSRY AFATAHIHGE IYRRRGLLTS EGKEIKNKEE

ILALLKALFL PKRLSIIHCP GHQKGHSAEA RGNRMADQAA RKAAITETPD

TSTLLIENSS PNSRLIN

>prod-cnc-aa (SEQ ID NO: 8)

MGGSHHHHHH GMASMTGGQQ MGRDLYDDDD KHMTLNIEDE HRLHETSKEP

DVSLGSTWLS DFPQAWAETG GMGLAKRQAP LIIPLKATAT PVSIKQYPMS

QEARQGIKPH IQRLLDQGIL VPCQSPWNTP LLPVKKPGTN DYRPVQDLRE

VNKRVEDIHP TVPNPYNLLS SLPPSHQWYT VLDLKDAFFC LRLHPKSQPL

FAFEWRDPEM GISGQLTWTR LPQGFKNSPT LFDEALRRDL ADFRIQHPDL

ILLQYVDDLL LAATTEEDCE QGTRALLQTL GELGYRASAK KAQICQKEVK

YLGYLLKEGQ RWLTEARKET VMKQPTPKTP RQLREFLGKA GFCRLWIPGF

AEMAAPLYPL TKTGTLFNWG PDQQKAFQEI KQALLTAPAL GLPDLTKPFE

LFVDEKQGVA KGVLTQKLGP WRRPVAYLSK KLDPVAAGWP PCLRMVAAIA

VLVKDADKLT MGQPLVILAP HAVEALIKQP PDRWLSNARM THYQALLLDT

DRVQFGPVVA LNPATLLPLP EEGLQHNCLD ILAEAHGTRP DLTDQPLPDA

DHTWYTGGSS FLQEGQRKAG AAVTTETEVI WAKALPAGTS AQRAQLIALT

QALKMAEGKK LNVYTNSRYA FATAHIHGEI YRRRGLLTSE GKEIKNKEEI

LALLKALFLP KRLSIIHCPG HQKGDSAEAR GNRMADQAAR KAAITETPDT

STLLIENSSP NSRLIN

>prod-cmi-aa (SEQ ID NO: 9)

MGGSHHHHHH GMASMTGGQQ MGRDLYDDDD KHMTLNIEDE HRLHETSKEP

DVSLGSMTWL SDFPQAWAET GGMGLAVRQA PLIIPLKATA TPVSIKQYPM

SQEARLGIKP HIQRLLDQGI LVPCQSPWNT PLLPVKKPGT NDYRPVQDLR

EVNKRVEDIH PTVPNPYNLL SSLPPSHQWY TVLDLKDAFF CLRLHPTSQP

LFAFEWRDPE MGISGQLTWT RLPQGFKNSP TLFDEALRRD LADFRIQHPD

LILLQYVDDL LLAATTEEDC QQGTRALLQT LGNLGYRASA KKAQICQKQV

KYLGYLLKEG QRWLTEARKE TVMKQPTPKT PRQLREFLGK AGNCRLWIPG

FAEMAAPLYP LTKTGTLFNW GPDQQKAFQE IKQALLTAPA LGLPDLTKPF

ELFVDEKQGY AKGVLTQKLG PWRRPVAYLS KKLDPVAAGW PPCLRMVAAI

AVLVKDADKL TMGQPLVILA PHAVEALIKQ PPDRWLSNAR MTHYQALLLD

TDRVQFGPVV ALNPATLLPL PEEGLQHNCL DILAEAHGTR PDLTDQPLPD

ADHTWYTGGS SLLQEGQRKA GAAVTTETEV IWAKALPAGT SAQRAQLIAL

TQALKMAEGK KLNVYTNSRY AFATAHIHGE IYRRRGLLTS EGKEIKNKEE

ILALLKALFL PKRLSIIHCP GHQKGHSAEA RGNRMADQAA RKAAITETPD

TSTLLIENSS PNSRLIN

-continued

>prod-bnb-aa (SEQ ID NO: 10)

MGGSHHHHHH GMASMTGGQQ MGRDLYDDDD KHMTLNIEDE HRLHETSKEP

DVSLGSTWLS DFPQAWAETG GMGLAVRQAP LIIPLKATAT PVSIKQYPMS

QEARQGIKPH IQRLLDQGIL VPCQSPWNTP LLPVKKPGTN DYRPVQDLRE

VNKRVEDIHP TVPNPYNLLS SLPPSHQWYT VLDLKDAFFC LRLHPKSQPL

FAFEWRDPEM GISGQLTWTR LPQGFKNSPT LFDEALRRDL ADFRIQHPDL

ILLQYVDDLL LAATTEEDCQ QGTRALLQTL GELGYRASAK KAQICQKQVK

YLGYLLKEGQ RWLTEARKET VMKQPTPKTP RQLREFLGKA GNCRLWIPGF

AEMAAPLYPL TKTGTLFNWG PDQQKAFQEI KQALLTAPAL GLPDLTKPFE

LFVDEKQGYA KGVLTQKLGP WRRPVAYLSK KLDPVAAGWP PCLRMVAAIA

VLVKDADKLT MGQPLVILAP HAVEALIKQP PDRWLSNARM THYQALLLDT

DRVQFGPVVA LNPATLLPLP EEGLQHNCLD ILAEAHGTRP DLTDQPLPDA

DHTWYTGGSS LLQEGQRKAG AAVTTETEVI WAKALPAGTS AQRAQLIALT

QALKMAEGKK LNVYTNSRYA FATAHIHGEI YRRRGLLTSE GKEIKNKEEI

LALLKALFLP KRLSIIHCPG HQKGDSAEAR GNRMADQAAR KAAITETPDT

STLLIENSSP NSRLIN

>prod-bsc-aa (SEQ ID NO: 11)

MGGSHHHHHH GMASMTGGQQ MGRDLYDDDD KHMTLNIEDE HRLHETSKEP

DVSLGSTWLT DFPQAWAETG GMGLAKRQPP IIIPLKPTAT PVWIKQYPMS

KEARQGIKPH IQRLLDQGIL VPCQSPWNTP LLPVKKPGTN DYRPVQDLRE

VNKRVQDIHP TVPNPCNLLS SLPPSHQWYT VLDLKDAFFC LRLHPKSQPL

FAFEWRDPER GISGQLTWTR LPQGFKNSPT LFHEALRRDL ADFRTQHPDL

TLLQYVDDLL LAAETEEDCE QGTRDLLQTL GELGYRASAK KAQICQQEVT

YLGYILKEGQ RWLSEARKET VMKQPTPKTP RQLREFLGKA GFCRLWIPGF

AEMAAPLYPL TKTGTLFQWG EEQQKAFDDI KRALLTAPAL GLPDLTKPFE

LFVDEKQGFA KGVLTQKLGP WRRPVAYLSK KLDPVAAGWP PCLRMIAAIA

VLVKDADKLT MGQPLTILAP HAVESLIKQP PDRWLSNARM THYQALLLDT

DRVQFGPVVA LNPATLLPLP EEGLQHNCLD ILAEAHGTRP DLTDQPLPDA

EHTWYTGGSS FLQEGQRKAG AAVTTETEVI WASALPPGTS AQRAQLIALT

QALKMAEGKK LNVYTNSRYA FATAHIHGEI YRRRGLLTSE GKEIKNKEEI

LELLKALWLP KKLAIIHCPG HQKGDSAEAR GNRMADQAAR EAAITETPDT

STLLIENSSP NSRLIN

>prod-csd-aa (SEQ ID NO: 12)

MGGSHHHHHH GMASMTGGQQ MGRDLYDDDD KHMTLNIEDE HRLHETSKEP

DVSLGSTWLT DFPQAWAETG GMGLAKRQPP IIIPLKPTAT PVWIKQYPMS

KEARQGIKPH IQRLLDQGIL VPCQSPWNTP LLPVKKPGTN DYRPVQDLRE

VNKRVQDIHP TVPNPCNLLS SLPPSHQWYT VLDLKDAFFC LRLHPKSQPL

FAFEWRDPER GISGQLTWTR LPQGFKNSPT LFHEALRRDL ADFRTQHPDL

TLLQYVDDLL LAAETEEDCE QGTRDLLQTL GELGYRASAK KAQICQQEVT

YLGYILKEGQ RWLSEARKET VLKQPTPKTP RQLREFLGKA GNCRLWIPGF

-continued

AEMAAPLYPL TKTGTLFQWG EEQQKAFDDI KRALLTAPAL GLPDLTKPFE

LFVDEKQGFA KGVLTQKLGP WRRPVAYLSK KLDPVAAGWP PCLRMIAAIA

VLVKDADKLT MGQPLTILAP HAVESLIKQP PDRWLSNARM THYQALLLDT

DRVQFGPVVA LNPATLLPLP EEGLQHNCLD ILAEAHGTRP DLTDQPLPDA

EHTWYTGGSS FLQEGQRKAG AAVTTETEVI WASALPPGTS AQRAQLIALT

QALKMAEGKK LNVYTNSRYA FATAHIHGEI YRRRGLLTSE GKEIKNKEEI

LELLKALWLP KKLAIIHCPG HQKGDSAEAR GNRMADQAAR EAAITETPDT

STLLIENSSP NSRLIN

>prod-dsf-aa (SEQ ID NO: 13)

MGGSHHHHHH GMASMTGGQQ MGRDLYDDDD KHMTLNIEDE HRLHETSKEP

DVSLGSTWLS DFPQAWAETG GMGLAKRQAP LIIPLKPTAT PVWIKQYPMS

QEARQGIKPH IQRLLDQGIL VPCQSPWNTP LLPVKKPGTN DYRPVQDLRE

VNKRVEDIHP TVPNPYNLLS SLPPSHQWYT VLDLKDAFFC LRLHPKSQPL

FAFEWRDPEM GISGQLTWTR LPQGFKNSPT LFHEALHRDL ADFRIQHPDL

ILLQYVDDLL LAATTEEDCE QGTRALLQTL GELGYRASAK KAQICQKEVT

YLGYLLKEGQ RWLTEARKET VMKQPTPKTP RQLREFLGTA GFCRLWIPGF

AEMAAPLYPL TKTGTLFNWG PEQQKAFQEI KQALLTAPAL GLPDLTKPFE

LFVDEKQGFA KGVLTQKLGP WRRPVAYLSK KLDPVAAGWP PCLRMVAAIA

VLVKDADKLT MGQPLTILAP HAVEALIKQP PDRWLSNARM THYQALLLDT

DRVQFGPVVA LNPATLLPLP EEGLQHNCLD ILAEAHGTRP DLTDQPLPDA

DHTWYTGGSS FLQEGQRKAG AAVTTETEVI WAKALPPGTS AQRAQLIALT

QALKMAEGKK LNVYTNSRYA FATAHIHGEI YRRRGLLTSE GKEIKNKEEI

LALLKALWLP KRLSIIHCPG HQKGDSAEAR GNRMADQAAR EAAITETPDT

STLLIENSSP NSRLIN

>prod-blh (SEQ ID NO: 14)

MGGSHHHHHHGMASMTGGQQMGRDLYDDDDKHMTLNIEDEHRLHETSKEPD

VSLGSTWLSDFPQAWAETGGMGLAVRQAPLIIPLKATSTPVSIKQYPMSQEARLGIKPHI

QRLLDQGILVPCQSPWNTPLLPVKKPGTNDYRPVQDLREVNKRVEDIHPTVPNPYNLLS

GLPPSHQWYTVLDLKDAFFCLRLHPTSQPLFAFEWRDPEMGISGQLTWTRLPQGFKNSP

TLFDEALRRDLADFRIQHPDLILLQYVDDLLLAATSELDCQQGTRALLQTLGNLGYRAS

AKKAQICQKQVKYLGYLLKEGQRWLTEARKETVMGQPTPKTPRQLREFLGKAGNCRL

WIPGFAEMAAPLYPLTKTGTLFNWGPDQQKAYQEIKQALLTAPALGLPDLTKPFELFVD

EKQGYAKGVLTQKLGPWRRPVAYLSKKLDPVAAGWPPCLRMVAAIAVLTKDAGKLT

MGQPLVILAPHAVEALVKQPPDRWLSNARMTHYQALLLDTDRVQFGPVVALNPATLLP

LPEEGLQHNCLDILAEAHGTRPDLTDQPLPDADHTWYTGGSSLLQEGQRKAGAAVTTE

TEVIWAKALPAGTSAQRAQLIALTQALKMAEGKKLNVYTNSRYAFATAHIHGEIYRRR

GLLTSEGKEIKNKDEILALLKALFLPKRLSIIHCPGHQKGHSAEARGNRMADQAARKAAI

TETPDTSTLL

>prod-ajw (SEQ ID NO: 15)

MGGSHHHHHHGMASMTGGQQMGRDLYDDDDKHMTLNIEDEHRLHETSKEPD

VSLGSTWLSDFPQAWAETGGMGLAVRQAPLIIPLKATSTPVSIKQYPMSQEARQGIKPHI

-continued

```
QRLLDQGILVPCQSPWNTPLLPVKKPGTNDYRPVQDLREVNKRVEDIHPTVPNPYNLLS
SLPPSHQWYTVLDLKDAFFCLRLHPKSQPLFAFEWRDPEMGISGQLTWTRLPQGFKNSP
TLFDEALHRDLADFRIQHPDLILLQYVDDLLLAATTEEDCQQGTRALLQTLGELGYRAS
AKKAQICQKQVKYLGYLLKEGQRWLTEARKETVMKQPTPKTPRQLREFLGTAGFCRL
WIPGFAEMAAPLYPLTKTGTLFNWGPDQQKAFQEIKQALLTAPALGLPDLTKPFELFVD
EKQGYAKGVLTQKLGPWRRPVAYLSKKLDPVAAGWPPCLRMVAAIAVLVKDADKLT
MGQPLVILAPHAVEALIKQPPDRWLSNARMTHYQALLLDTDRVQFGPVVALNPATLLP
LPEEGLQHNCLDILAEAHGTRPDLTDQPLPDADHTWYTGGSSLLQEGQRKAGAAVTTE
TEVIWAKALPAGTSAQRAQLIALTQALKMAEGKKLNVYTNSRYAFATAHIHGEIYRRR
GLLTSEGKEIKNKEEILALLKALFLPKRLSIIHCPGHQKGDSAEARGNRMADQAARKAAI
TETPDTSTLLIENSSPNSRLIN
```

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A reverse transcriptase comprising an amino acid sequence having at least 98% sequence identity with the reverse transcriptase of SEQ ID NO: 1, and at least one amino acid substitution selected from:

S at position 56 substituted with G, A, V, L, or I;

G at position 138 substituted with S, C, T, or M;

S at position 232 substituted with C, T, or M;

L at position 234 substituted with D, E, N, Q;

G at position 290 substituted with H, K, or R;

Y at position 344 substituted with F or M;

T at position 420 substituted with G, A, V, L, or I;

G at position 424 substituted with D, E, N, or Q;

V at position 444 substituted with G, A, L, or I; and

D at position 615 substituted with E, N, or Q.

2. The reverse transcriptase of claim 1, comprising at least three amino acid substitutions at three different positions selected from:

S at position 56 substituted with G, A, V, L, or I;

G at position 138 substituted with S, C, T, or M;

S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I; and
D at position 615 substituted with E, N, or Q.

3. The reverse transcriptase of claim 1, comprising:
S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I; and
D at position 615 substituted with E, N, or Q.

4. The reverse transcriptase of claim 1, wherein the amino acid substitution is selected from S56G, G138S, S232M, L234N, G290K, Y344M, T420A, G424D, V444G, and D615N.

5. The reverse transcriptase of claim 1, comprising the following amino acid substitutions: S56G, G138S, S232M, L234N, G290K, Y344M, T420A, G424D, V444G, and D615N.

6. The reverse transcriptase of claim 5, further comprising the following amino acid substitutions: L72Q, T163K, H204R, T306K, G524D, D583N, and E562Q.

7. The reverse transcriptase of claim 1, wherein the amino acid substitution is selected from S56A, G138S, S232T, L234E, G290K, Y344F, T420V, G424D, V444I, and D615E.

8. The reverse transcriptase of claim 1, comprising the following amino acid substitutions: S56A, G138S, S232T, L234E, G290K, Y344F, T420V, G424D, V444I, and D615E.

9. The reverse transcriptase of claim 8, further comprising the following amino acid substitutions: L72Q, T163K, H204R, N249E, T306K, G524D, D583N, E562Q and H642D.

10. The reverse transcriptase of claim 1 further comprising at least one amino acid substitution selected from:
L at position 72 substituted with Q or R;
T at position 163 substituted with K;
H at position 204 substituted with K or R;
N at position 249 substituted with E or D;
T at position 306 substituted with H, K, or R;
D at position 524 substituted with G, A, V, L, or I;
E at position 562 substituted with D, N, or Q;
D at position 583 substituted with E, N, or Q; and
H at position 642 substituted with D, E, N, or Q.

11. The reverse transcriptase of claim 1, comprising at least one additional amino acid substitution selected from L72Q, T163K, H204R, N249E, T306K, G524D, D583N, E562Q, and H642D.

12. The reverse transcriptase of claim 1, comprising the following amino acid substitutions: L72Q, T163K, H204R, N249E, T306K, G524D, D583N, E562Q, and H642D.

13. The reverse transcriptase of claim 1 comprising the amino acid sequence of SEQ ID NO: 1 that comprises:
S at position 56 substituted with G, A, V, L, or I;
G at position 138 substituted with S, C, T, or M;
S at position 232 substituted with C, T, or M;
L at position 234 substituted with D, E, N, Q;
G at position 290 substituted with H, K, or R;
Y at position 344 substituted with F or M;
T at position 420 substituted with G, A, V, L, or I;
G at position 424 substituted with D, E, N, or Q;
V at position 444 substituted with G, A, L, or I; and
D at position 615 substituted with E, N, or Q.

14. The reverse transcriptase of claim 13, wherein the activity of the reverse transcriptase at temperatures of 65° C. or greater is at least 50% of the reverse transcription activity of the reverse transcriptase shown in SEQ ID NO: 2 at 42° C.

15. The reverse transcriptase of claim 13, wherein the activity of the reverse transcriptase is improved compared to the reverse transcriptase shown in SEQ ID NO: 2 in the presence of inhibitors of reverse transcription.

16. A reverse transcriptase comprising an amino acid sequence having at least 95% sequence identity with the reverse transcriptase of SEQ ID NO: 1, and at least one amino acid substitution selected from:
S at position 56 substituted with G, A, V, L, or I;
G at position 138 substituted with S, C, T, or M;
S at position 232 substituted with C, T, or M;
T at position 420 substituted with G, A, V, L, or I;
G at position 424 substituted with D, E, N, or Q; and
V at position 444 substituted with G, A, L, or I.

17. A reverse transcriptase comprising an amino acid sequence having at least 98% identity to amino acids 34-716 of SEQ ID NO: 4.

18. The reverse transcriptase of claim 17, comprising amino acids 34-716 of SEQ ID NO: 4.

19. A reverse transcriptase comprising an amino acid sequence having at least 98% identity to amino acids 34-717 of SEQ ID NO: 5.

20. The reverse transcriptase of claim 19, comprising amino acids 34-717 of SEQ ID NO: 5.

21. A reverse transcriptase comprising an amino acid sequence having at least 95% identity to amino acids 34-716 of SEQ ID NO: 6.

22. The reverse transcriptase of claim 21, comprising amino acids 34-716 of SEQ ID NO: 6.

* * * * *

SEQUENCE LISTING

```
Sequence total quantity: 15
SEQ ID NO: 1           moltype = AA  length = 671
FEATURE                Location/Qualifiers
source                 1..671
                       mol_type = protein
                       organism = Murine leukemia virus
SEQUENCE: 1
TLNIEDEHRL HETSKEPDVS LGSTWLSDFP QAWAETGGMG LAVRQAPLII PLKATSTPVS  60
IKQYPMSQEA RLGIKPHIQR LLDQGILVPC QSPWNTPLLP VKKPGTNDYR PVQDLREVNK  120
RVEDIHPTVP NPYNLLSGLP PSHQWYTVLD LKDAFFCLRL HPTSQPLFAF EWRDPEMGIS  180
GQLTWTRLPQ GFKNSPTLFD EALHRDLADF RIQHPDLILL QYVDDLLLAA TSELDCQQGT  240
RALLQTLGNL GYRASAKKAQ ICQKQVKYLG YLLKEGQRWL TEARKETVMG QPTPKTPRQL  300
REFLGTAGFC RLWIPGFAEM AAPLYPLTKT GTLFNWGPDQ QKAYQEIKQA LLTAPALGLP  360
DLTKPFELFV DEKQGYAKGV LTQKLGPWRR PVAYLSKKLD PVAAGWPPCL RMVAAIAVLT  420
KDAGKLTMGQ PLVILAPHAV EALVKQPPDR WLSNARMTHY QALLLDTDRV QFGPVVALNP  480
ATLLPLPEEG LQHNCLDILA EAHGTRPDLT DQPLPDADHT WYTDGSSLLQ EGQRKAGAAV  540
TTETEVIWAK ALPAGTSAQR AELIALTQAL KMAEGKKLNV YTDSRYAFAT AHIHGEIYRR  600
RGLLTSEGKE IKNKDEILAL LKALFLPKRL SIIHCPGHQK GHSAEARGNR MADQAARKAA  660
ITETPDTSTL L                                                       671

SEQ ID NO: 2           moltype = AA  length = 704
FEATURE                Location/Qualifiers
REGION                 1..704
                       note = Synthetic
source                 1..704
                       mol_type = protein
                       organism = synthetic construct
SEQUENCE: 2
MGGSHHHHHH GMASMTGGQQ MGRDLYDDDD KHMTLNIEDE HRLHETSKEP DVSLGSTWLS  60
DFPQAWAETG GMGLAVRQAP LIIPLKATST PVSIKQYPMS QEARLGIKPH IQRLLDQGIL  120
VPCQSPWNTP LLPVKKPGTN DYRPVQDLRE VNKRVEDIHP TVPNPYNLLS GLPPSHQWYT  180
VLDLKDAFFC LRLHPTSQPL FAFEWRDPEM GISGQLTWTR LPQGFKNSPT LFDEALHRDL  240
ADFRIQHPDL ILLQYVDDLL LAATSELDCQ QGTRALLQTL GNLGYRASAK KAQICQKQVK  300
YLGYLLKEGQ RWLTEARKET VMGQPTPKTP RQLREFLGTA GFCRLWIPGF AEMAAPLYPL  360
TKTGTLFNWG PDQQKAYQEI KQALLTAPAL GLPDLTKPFE LFVDEKQGYA KGVLTQKLGP  420
WRRPVAYLSK KLDPVAAGWP PCLRMVAAIA VLTKDAGKLT MGQPLVILAP HAVEALVKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKDEI LALLKALFLP  660
```

-continued

```
KRLSIIHCPG HQKGHSAEAR GNRMADQAAR KAAITETPDT STLL                    704

SEQ ID NO: 3           moltype = DNA  length = 2115
FEATURE                Location/Qualifiers
misc_feature           1..2115
                       note = Synthetic
source                 1..2115
                       mol_type = other DNA
                       organism = synthetic construct
SEQUENCE: 3
atggggggtt ctcatcatca tcatcatcat ggtatggcta gcatgactgg tggacagcaa  60
atgggtcggg atctgtacga cgatgacgat aagcatatga ccctaaatat agaagatgag  120
caccggctac atgagacctc aaaagagcca gatgtttctc tagggtccac atggttatcg  180
gatttcccgc aagcttgggc tgaaacgggg ggtatggggc ttgctgtacg ccaggcgccc  240
cttattattc ctcttaaggc aacaagcacc cccgtcagca tcaaacaata ccccatgtca  300
caagaagcgc gtttgggtat taaaccgcac attcaacgct tgctggacca agggatcctt  360
gtcccctgtc agtctccatg gaacacgccg ctgttaccgg tcaagaagcc tggtacaaac  420
gactaccgtc ctgtacagga tttgcgcgag gtaaataagc gtgtagagga tatccacccc  480
accgtgccca acccatacaa cttgttgtct ggtttaccgc cttcacatca gtggtatacg  540
gtccttgatt tgaaagatgc atttttctgc ctgcgcttgc accctacgtc tcagccactg  600
ttcgcattcg agtggcgcga ccctgaaatg ggtatcagtg gtcagttaac ctggacacgc  660
ttaccgcaag gtttcaagaa tagcccgacc ttattcgatg aagcacttca ccgcgatctt  720
gccgatttcc gcatccagca cccggatctt attttgttgc agtacgtaga cgacctgttg  780
ttggcagcca cgtcggaatt ggattgtcag caaggaacac gcgcgttact gcaaactctg  840
ggtaatttgg gctaccgtgc ctccgcaaag aaagcgcaga tctgccaaaa gcaagtaaaa  900
tacttaggat atttattgaa ggagggccag cgttggctta cagaagctcg caaagaaact  960
gtgatgggac aacctacgcc taaaactcct cgtcagcttc gcgaattcct gggaacagcg  1020
gggttctgtc gcctgtggat tcctggtttt gcagagatgg cggcgcccct ttacccactg  1080
accaaaacag ggacattatt taactggggt cccgatcagc agaaggccta tcaggagatc  1140
aagcaggctt tacttacagc gccagcctta gggttaccgg accttacgaa gccctttgag  1200
ttattcgtcg acgagaaaca gggctatgca aagggtgtac tgacccagaa gttggggccg  1260
tggcgtcgcc cggtcgccta tttgtcgaaa aaactggatc ccgtggcggc cgggtggcca  1320
ccttgcctgc gtatggttgc agctattgct gtattaacaa aagacgcagg aaaattaacg  1380
atgggacaac cgttagtcat tcttgcgccg cacgcagtag aagcactggt aaagcaaccg  1440
cccgatcgct ggttatcgaa cgcgcgcatg acgcactatc aggcgttgtt acttgataca  1500
gatcgtgtac agtttggccc tgtcgttgca ttgaacccag ccacgctgtt acctcttccg  1560
gaagaaggat tacaacacaa ctgtctggac atcctggcgg aagctcatgg aacccgccct  1620
gacttgacag accaaccgtt acccgacgct gatcatacct ggtataccgg gggttcgtcg  1680
cttttgcagg aagggcaacg taaggcaggt gcagccgtaa cgaccgagac cgaagtcatc  1740
tgggccaagg ccttgccagc ggggactagt gcccagcgtg cccaattaat tgcccttacg  1800
caggcattaa agatggctga aggaaaaaag ctgaatgtat acactaacag ccgctacgcg  1860
ttcgcgacag cgcatattca tggagagatc taccgtcgcc gcggacttct tacctccgag  1920
ggtaaggaga ttaagaacaa agatgagatt ctggctttgt tgaaggcgtt gtttttgccc  1980
aaacgtttgt caatcattca ctgtcccggg catcaaaaag ggcacagcgc cgaggcccgt  2040
ggtaaccgta tggcagacca ggccgcacgt aaagcagcca ttacggagac acctgatacg  2100
agtacgttac tttaa                                                   2115

SEQ ID NO: 4           moltype = AA  length = 716
FEATURE                Location/Qualifiers
REGION                 1..716
                       note = Synthetic
source                 1..716
                       mol_type = protein
                       organism = synthetic construct
SEQUENCE: 4
MGGSHHHHHH GMASMTGGQQ MGRDLYDDDD KHMTLNIEDE HRLHETSKEP DVSLGSTWLS  60
DFPQAWAETG GMGLAVRQAP LIIPLKATAT PVSIKQYPMS QEARQGIKPH IQRLLDQGIL  120
VPCQSPWNTP LLPVKKPGTN DYRPVQDLRE VNKRVEDIHP TVPNPYNLLS SLPPSHQWYT  180
VLDLKDAFFC LRLHPKSQPL FAFEWRDPEM GISGQLTWTR LPQGFKNSPT LFDEALRRDL  240
ADFRIQHPDL ILLQYVDDLL LAATTEEDCQ QGTRALLQTL GELGYRASAK KAQICQKQVK  300
YLGYLLKEGQ RWLTEARKET VMKQPTPKTP RQLREFLGKA GFCRLWIPGF AEMAAPLYPL  360
TKTGTLFNWG PDQQKAFQEI KQALLTAPAL GLPDLTKPFE LFVDEKQGYA KGVLTQKLGP  420
WRRPVAYLSK KLDPVAAGWP PCLRMVAAIA VLVKDADKLT MGQPLVILAP HAVEALIKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKEEI LALLKALFLP  660
KRLSIIHCPG HQKGDSAEAR GNRMADQAAR KAAITETPDT STLLIENSSP NSRLIN      716

SEQ ID NO: 5           moltype = AA  length = 717
FEATURE                Location/Qualifiers
REGION                 1..717
                       note = Synthetic
source                 1..717
                       mol_type = protein
                       organism = synthetic construct
SEQUENCE: 5
MGGSHHHHHH GMASMTGGQQ MGRDLYDDDD KHMTLNIEDE HRLHETSKEP DVSLGSMTWL  60
SDFPQAWAET GGMGLAVRQA PLIIPLKATA TPVSIKQYPM SQEARLGIKP HIQRLLDQGI  120
LVPCQSPWNT PLLPVKKPGT NDYRPVQDLR EVNKRVEDIH PTVPNPYNLL SSLPPSHQWY  180
```

-continued

```
TVLDLKDAFF CLRLHPTSQP LFAFEWRDPE MGISGQLTWT RLPQGFKNSP TLFDEALHRD  240
LADFRIQHPD LILLQYVDDL LLAATTEEDC QQGTRALLQT LGNLGYRASA KKAQICQKQV  300
KYLGYLLKEG QRWLTEARKE TVMKQPTPKT PRQLREFLGT AGFCRLWIPG FAEMAAPLYP  360
LTKTGTLFNW GPDQQKAFQE IKQALLTAPA LGLPDLTKPF ELFVDEKQGY AKGVLTQKLG  420
PWRRPVAYLS KKLDPVAAGW PPCLRMVAAI AVLVKDADKL TMGQPLVILA PHAVEALIKQ  480
PPDRWLSNAR MTHYQALLLD TDRVQFGPVV ALNPATLLPL PEEGLQHNCL DILAEAHGTR  540
PDLTDQPLPD ADHTWYTGGS SLLQEGQRKA GAAVTTETEV IWAKALPAGT SAQRAQLIAL  600
TQALKMAEGK KLNVYTNSRY AFATAHIHGE IYRRRGLLTS EGKEIKNKEE ILALLKALFL  660
PKRLSIIHCP GHQKGHSAEA RGNRMADQAA RKAAITETPD TSTLLIENSS PNSRLIN     717

SEQ ID NO: 6            moltype = AA  length = 716
FEATURE                 Location/Qualifiers
REGION                  1..716
                        note = Synthetic
source                  1..716
                        mol_type = protein
                        organism = synthetic construct
SEQUENCE: 6
MGGSHHHHHH GMASMTGGQQ MGRDLYDDDD KHMTLNIEDE HRLHETSKEP DVSLGSTWLT  60
DFPQAWAETG GMGLAKRQPP IIIPLKPTAT PVWIKQYPMS KEARQGIKPH IQRLLDQGIL  120
VPCQSPWNTP LLPVKKPGTN DYRPVQDLRE VNKRVQDIHP TVPNPCNLLS SLPPSHQWYT  180
VLDLKDAFFC LRLHPKSQPL FAFEWRDPER GISGQLTWTR LPQGFKNSPT LFHEALHRDL  240
ADFRTQHPDL TLLQYVDDLL LAAETEEDCE QGTRDLLQTL GELGYRASAK KAQICQQEVT  300
YLGYILKEGQ RWLSEARKET VMKQPTPKTP RQLREFLGTA GFCRLWIPGF AEMAAPLYPL  360
TKTGTLFQWG EEQQKAFDDI KRALLTAPAL GLPDLTKPFE LFVDEKQGFA KGVLTQKLGP  420
WRRPVAYLSK KLDPVAAGWP PCLRMIAAIA VLVKDADKLT MGQPLTILAP HAVESLIKQP  480
PDRWLSNARM THYQALLLDT DRVQFGPVVA LNPATLLPLP EEGLQHNCLD ILAEAHGTRP  540
DLTDQPLPDA EHTWYTGGSS FLQEGQRKAG AAVTTETEVI WASALPPGTS AQRAQLIALT  600
QALKMAEGKK LNVYTNSRYA FATAHIHGEI YRRRGLLTSE GKEIKNKEEI LELLKALWLP  660
KKLAIIHCPG HQKGDSAEAR GNRMADQAAR EAAITETPDT STLLIENSSP NSRLIN      716

SEQ ID NO: 7            moltype = AA  length = 717
FEATURE                 Location/Qualifiers
REGION                  1..717
                        note = Synthetic
source                  1..717
                        mol_type = protein
                        organism = synthetic construct
SEQUENCE: 7
MGGSHHHHHH GMASMTGGQQ MGRDLYDDDD KHMTLNIEDE HRLHETSKEP DVSLGSMTWL  60
SDFPQAWAET GGMGLAVRQA PLIIPLKATA TPVSIKQYPM SQEARLGIKP HIQRLLDQGI  120
LVPCQSPWNT PLLPVKKPGT NDYRPVQDLR EVNKRVEDIH PTVPNPYNLL SSLPPSHQWY  180
TVLDLKDAFF CLRLHPTSQP LFAFEWRDPE MGISGQLTWT RLPQGFKNSP TLFDEALRRD  240
LADFRIQHPD LILLQYVDDL LLAATTEEDC QQGTRALLQT LGNLGYRASA KKAQICQKQV  300
KYLGYLLKEG QRWLTEARKE TVMKQPTPKT PRQLREFLGK AGFCRLWIPG FAEMAAPLYP  360
LTKTGTLFNW GPDQQKAFQE IKQALLTAPA LGLPDLTKPF ELFVDEKQGY AKGVLTQKLG  420
PWRRPVAYLS KKLDPVAAGW PPCLRMVAAI AVLVKDADKL TMGQPLVILA PHAVEALIKQ  480
PPDRWLSNAR MTHYQALLLD TDRVQFGPVV ALNPATLLPL PEEGLQHNCL DILAEAHGTR  540
PDLTDQPLPD ADHTWYTGGS SLLQEGQRKA GAAVTTETEV IWAKALPAGT SAQRAQLIAL  600
TQALKMAEGK KLNVYTNSRY AFATAHIHGE IYRRRGLLTS EGKEIKNKEE ILALLKALFL  660
PKRLSIIHCP GHQKGHSAEA RGNRMADQAA RKAAITETPD TSTLLIENSS PNSRLIN     717

SEQ ID NO: 8            moltype = AA  length = 716
FEATURE                 Location/Qualifiers
REGION                  1..716
                        note = Synthetic
source                  1..716
                        mol_type = protein
                        organism = synthetic construct
SEQUENCE: 8
MGGSHHHHHH GMASMTGGQQ MGRDLYDDDD KHMTLNIEDE HRLHETSKEP DVSLGSTWLS  60
DFPQAWAETG GMGLAKRQAP LIIPLKATAT PVSIKQYPMS QEARQGIKPH IQRLLDQGIL  120
VPCQSPWNTP LLPVKKPGTN DYRPVQDLRE VNKRVEDIHP TVPNPYNLLS SLPPSHQWYT  180
VLDLKDAFFC LRLHPKSQPL FAFEWRDPEM GISGQLTWTR LPQGFKNSPT LFDEALRRDL  240
ADFRIQHPDL ILLQYVDDLL LAATTEEDCE QGTRALLQTL GELGYRASAK KAQICQKEVK  300
YLGYLLKEGQ RWLTEARKET VMKQPTPKTP RQLREFLGKA GFCRLWIPGF AEMAAPLYPL  360
TKTGTLFNWG PDQQKAFQEI KQALLTAPAL GLPDLTKPFE LFVDEKQGVA KGVLTQKLGP  420
WRRPVAYLSK KLDPVAAGWP PCLRMVAAIA VLVKDADKLT MGQPLVILAP HAVEALIKQP  480
PDRWLSNARM THYQALLLDT DRVQFGPVVA LNPATLLPLP EEGLQHNCLD ILAEAHGTRP  540
DLTDQPLPDA DHTWYTGGSS FLQEGQRKAG AAVTTETEVI WAKALPAGTS AQRAQLIALT  600
QALKMAEGKK LNVYTNSRYA FATAHIHGEI YRRRGLLTSE GKEIKNKEEI LALLKALFLP  660
KRLSIIHCPG HQKGDSAEAR GNRMADQAAR KAAITETPDT STLLIENSSP NSRLIN      716

SEQ ID NO: 9            moltype = AA  length = 717
FEATURE                 Location/Qualifiers
REGION                  1..717
                        note = Synthetic
source                  1..717
                        mol_type = protein
```

```
                         organism = synthetic construct
SEQUENCE: 9
MGGSHHHHHH GMASMTGGQQ MGRDLYDDDD KHMTLNIEDE HRLHETSKEP DVSLGSMTWL  60
SDFPQAWAET GGMGLAVRQA PLIIPLKATA TPVSIKQYPM SQEARLGIKP HIQRLLDQGI  120
LVPCQSPWNT PLLPVKKPGT NDYRPVQDLR EVNKRVEDIH PTVPNPYNLL SSLPPSHQWY  180
TVLDLKDAFF CLRLHPTSQP LFAFEWRDPE MGISGQLTWT RLPQGFKNSP TLFDEALRRD  240
LADFRIQHPD LILLQYVDDL LLAATTEEDC QQGTRALLQT LGNLGYRASA KKAQICQKQV  300
KYLGYLLKEG QRWLTEARKE TVMKQPTPKT PRQLREFLGK AGNCRLWIPG FAEMAAPLYP  360
LTKTGTLFNW GPDQQKAFQE IKQALLTAPA LGLPDLTKPF ELFVDEKQGY AKGVLTQKLG  420
PWRRPVAYLS KKLDPVAAGW PPCLRMVAAI AVLVKDADKL TMGQPLVILA PHAVEALIKQ  480
PPDRWLSNAR MTHYQALLLD TDRVQFGPVV ALNPATLLPL PEEGLQHNCL DILAEAHGTR  540
PDLTDQPLPD ADHTWYTGGS SLLQEGQRKA GAAVTTETEV IWAKALPAGT SAQRAQLIAL  600
TQALKMAEGK KLNVYTNSRY AFATAHIHGE IYRRRGLLTS EGKEIKNKEE ILALLKALFL  660
PKRLSIIHCP GHQKGHSAEA RGNRMADQAA RKAAITETPD TSTLLIENSS PNSRLIN     717

SEQ ID NO: 10            moltype = AA  length = 716
FEATURE                  Location/Qualifiers
REGION                   1..716
                         note = Synthetic
source                   1..716
                         mol_type = protein
                         organism = synthetic construct
SEQUENCE: 10
MGGSHHHHHH GMASMTGGQQ MGRDLYDDDD KHMTLNIEDE HRLHETSKEP DVSLGSTWLS  60
DFPQAWAETG GMGLAVRQAP LIIPLKATAT PVSIKQYPMS QEARQGIKPH IQRLLDQGIL  120
VPCQSPWNTP LLPVKKPGTN DYRPVQDLRE VNKRVEDIHP TVPNPYNLLS SLPPSHQWYT  180
VLDLKDAFFC LRLHPKSQPL FAFEWRDPEM GISGQLTWTR LPQGFKNSPT LFDEALRRDL  240
ADFRIQHPDL ILLQYVDDLL LAATTEEDCQ QGTRALLQTL GELGYRASAK KAQICQKQVK  300
YLGYLLKEGQ RWLTEARKET VMKQPTPKTP RQLREFLGKA GNCRLWIPGF AEMAAPLYPL  360
TKTGTLFNWG PDQQKAFQEI KQALLTAPAL GLPDLTKPFE LFVDEKQGYA KGVLTQKLGP  420
WRRPVAYLSK KLDPVAAGWP PCLRMVAAIA VLVKDADKLT MGQPLVILAP HAVEALIKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKEEI LALLKALFLP  660
KRLSIIHCPG HQKGDSAEAR GNRMADQAAR KAAITETPDT STLLIENSSP NSRLIN      716

SEQ ID NO: 11            moltype = AA  length = 716
FEATURE                  Location/Qualifiers
REGION                   1..716
                         note = Synthetic
source                   1..716
                         mol_type = protein
                         organism = synthetic construct
SEQUENCE: 11
MGGSHHHHHH GMASMTGGQQ MGRDLYDDDD KHMTLNIEDE HRLHETSKEP DVSLGSTWLT  60
DFPQAWAETG GMGLAKRQPP IIIPLKPTAT PVWIKQYPMS KEARQGIKPH IQRLLDQGIL  120
VPCQSPWNTP LLPVKKPGTN DYRPVQDLRE VNKRVQDIHP TVPNPCNLLS SLPPSHQWYT  180
VLDLKDAFFC LRLHPKSQPL FAFEWRDPER GISGQLTWTR LPQGFKNSPT LFHEALRRDL  240
ADFRTQHPDL TLLQYVDDLL LAAETEEDCE QGTRDLLQTL GELGYRASAK KAQICQQEVT  300
YLGYILKEGQ RWLSEARKET VMKQPTPKTP RQLREFLGKA GFCRLWIPGF AEMAAPLYPL  360
TKTGTLFQWG EEQQKAFDDI KRALLTAPAL GLPDLTKPFE LFVDEKQGFA KGVLTQKLGP  420
WRRPVAYLSK KLDPVAAGWP PCLRMIAAIA VLVKDADKLT MGQPLTILAP HAVESLIKQP  480
PDRWLSNARM THYQALLLDT DRVQFGPVVA LNPATLLPLP EEGLQHNCLD ILAEAHGTRP  540
DLTDQPLPDA EHTWYTGGSS FLQEGQRKAG AAVTTETEVI WASALPPGTS AQRAQLIALT  600
QALKMAEGKK LNVYTNSRYA FATAHIHGEI YRRRGLLTSE GKEIKNKEEI LELLKALWLP  660
KKLAIIHCPG HQKGDSAEAR GNRMADQAAR EAAITETPDT STLLIENSSP NSRLIN      716

SEQ ID NO: 12            moltype = AA  length = 716
FEATURE                  Location/Qualifiers
REGION                   1..716
                         note = Synthetic
source                   1..716
                         mol_type = protein
                         organism = synthetic construct
SEQUENCE: 12
MGGSHHHHHH GMASMTGGQQ MGRDLYDDDD KHMTLNIEDE HRLHETSKEP DVSLGSTWLT  60
DFPQAWAETG GMGLAKRQPP IIIPLKPTAT PVWIKQYPMS KEARQGIKPH IQRLLDQGIL  120
VPCQSPWNTP LLPVKKPGTN DYRPVQDLRE VNKRVQDIHP TVPNPCNLLS SLPPSHQWYT  180
VLDLKDAFFC LRLHPKSQPL FAFEWRDPER GISGQLTWTR LPQGFKNSPT LFHEALRRDL  240
ADFRTQHPDL TLLQYVDDLL LAAETEEDCE QGTRDLLQTL GELGYRASAK KAQICQQEVT  300
YLGYILKEGQ RWLSEARKET VLKQPTPKTP RQLREFLGKA GNCRLWIPGF AEMAAPLYPL  360
TKTGTLFQWG EEQQKAFDDI KRALLTAPAL GLPDLTKPFE LFVDEKQGFA KGVLTQKLGP  420
WRRPVAYLSK KLDPVAAGWP PCLRMIAAIA VLVKDADKLT MGQPLTILAP HAVESLIKQP  480
PDRWLSNARM THYQALLLDT DRVQFGPVVA LNPATLLPLP EEGLQHNCLD ILAEAHGTRP  540
DLTDQPLPDA EHTWYTGGSS FLQEGQRKAG AAVTTETEVI WASALPPGTS AQRAQLIALT  600
QALKMAEGKK LNVYTNSRYA FATAHIHGEI YRRRGLLTSE GKEIKNKEEI LELLKALWLP  660
KKLAIIHCPG HQKGDSAEAR GNRMADQAAR EAAITETPDT STLLIENSSP NSRLIN      716

SEQ ID NO: 13            moltype = AA  length = 716
```

-continued

```
FEATURE                Location/Qualifiers
REGION                 1..716
                       note = Synthetic
source                 1..716
                       mol_type = protein
                       organism = synthetic construct
SEQUENCE: 13
MGGSHHHHHH GMASMTGGQQ MGRDLYDDDD KHMTLNIEDE HRLHETSKEP DVSLGSTWLS  60
DFPQAWAETG GMGLAKRQAP LIIPLKPTAT PVWIKQYPMS QEARQGIKPH IQRLLDQGIL  120
VPCQSPWNTP LLPVKKPGTN DYRPVQDLRE VNKRVEDIHP TVPNPYNLLS SLPPSHQWYT  180
VLDLKDAFFC LRLHPKSQPL FAFEWRDPEM GISGQLTWTR LPQGFKNSPT LFHEALHRDL  240
ADFRIQHPDL ILLQYVDDLL LAATTEEDCE QGTRALLQTL GELGYRASAK KAQICQKEVT  300
YLGYLLKEGQ RWLTEARKET VMKQPTPKTP RQLREFLGTA GFCRLWIPGF AEMAAPLYPL  360
TKTGTLFNWG PEQQKAFQEI KQALLTAPAL GLPDLTKPFE LFVDEKQGFA KGVLTQKLGP  420
WRRPVAYLSK KLDPVAAGWP PCLRMVAAIA VLVKDADKLT MGQPLTILAP HAVEALIKQP  480
PDRWLSNARM THYQALLLDT DRVQFGPVVA LNPATLLPLP EEGLQHNCLD ILAEAHGTRP  540
DLTDQPLPDA DHTWYTGGSS FLQEGQRKAG AAVTTETEVI WAKALPPGTS AQRAQLIALT  600
QALKMAEGKK LNVYTNSRYA FATAHIHGEI YRRRGLLTSE GKEIKNKEEI LALLKALWLP  660
KRLSIIHCPG HQKGDSAEAR GNRMADQAAR EAAITETPDT STLLIENSSP NSRLIN      716

SEQ ID NO: 14          moltype = AA  length = 704
FEATURE                Location/Qualifiers
REGION                 1..704
                       note = Synthetic
source                 1..704
                       mol_type = protein
                       organism = synthetic construct
SEQUENCE: 14
MGGSHHHHHH GMASMTGGQQ MGRDLYDDDD KHMTLNIEDE HRLHETSKEP DVSLGSTWLS  60
DFPQAWAETG GMGLAVRQAP LIIPLKATST PVSIKQYPMS QEARLGIKPH IQRLLDQGIL  120
VPCQSPWNTP LLPVKKPGTN DYRPVQDLRE VNKRVEDIHP TVPNPYNLLS GLPPSHQWYT  180
VLDLKDAFFC LRLHPTSQPL FAFEWRDPEM GISGQLTWTR LPQGFKNSPT LFDEALRRDL  240
ADFRIQHPDL ILLQYVDDLL LAATSELDCQ QGTRALLQTL GNLGYRASAK KAQICQKQVK  300
YLGYLLKEGQ RWLTEARKET VMGQPTPKTP RQLREFLGKA GNCRLWIPGF AEMAAPLYPL  360
TKTGTLFNWG PDQQKAYQEI KQALLTAPAL GLPDLTKPFE LFVDEKQGYA KGVLTQKLGP  420
WRRPVAYLSK KLDPVAAGWP PCLRMVAAIA VLTKDAGKLT MGQPLVILAP HAVEALVKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKDEI LALLKALFLP  660
KRLSIIHCPG HQKGHSAEAR GNRMADQAAR KAAITETPDT STLL                  704

SEQ ID NO: 15          moltype = AA  length = 716
FEATURE                Location/Qualifiers
REGION                 1..716
                       note = Synthetic
source                 1..716
                       mol_type = protein
                       organism = synthetic construct
SEQUENCE: 15
MGGSHHHHHH GMASMTGGQQ MGRDLYDDDD KHMTLNIEDE HRLHETSKEP DVSLGSTWLS  60
DFPQAWAETG GMGLAVRQAP LIIPLKATST PVSIKQYPMS QEARQGIKPH IQRLLDQGIL  120
VPCQSPWNTP LLPVKKPGTN DYRPVQDLRE VNKRVEDIHP TVPNPYNLLS SLPPSHQWYT  180
VLDLKDAFFC LRLHPKSQPL FAFEWRDPEM GISGQLTWTR LPQGFKNSPT LFDEALHRDL  240
ADFRIQHPDL ILLQYVDDLL LAATTEEDCQ QGTRALLQTL GELGYRASAK KAQICQKQVK  300
YLGYLLKEGQ RWLTEARKET VMKQPTPKTP RQLREFLGTA GFCRLWIPGF AEMAAPLYPL  360
TKTGTLFNWG PDQQKAFQEI KQALLTAPAL GLPDLTKPFE LFVDEKQGYA KGVLTQKLGP  420
WRRPVAYLSK KLDPVAAGWP PCLRMVAAIA VLVKDADKLT MGQPLVILAP HAVEALIKQP  480
PDRWLSNARM THYQALLLDT DRVQFGPVVA LNPATLLPLP EEGLQHNCLD ILAEAHGTRP  540
DLTDQPLPDA DHTWYTGGSS LLQEGQRKAG AAVTTETEVI WAKALPAGTS AQRAQLIALT  600
QALKMAEGKK LNVYTNSRYA FATAHIHGEI YRRRGLLTSE GKEIKNKEEI LALLKALFLP  660
KRLSIIHCPG HQKGDSAEAR GNRMADQAAR KAAITETPDT STLLIENSSP NSRLIN      716
```